United States Patent [19]
Audia et al.

[11] Patent Number: 5,495,021
[45] Date of Patent: Feb. 27, 1996

[54] BENZO[F]QUINOLINONES

[75] Inventors: James E. Audia, Indianapolis; David E. Lawhorn, Greenfield; Leland O. Weigel, Indianapolis, all of Ind.

[73] Assignee: Eli Lilly and Company, Indianapolis, Ind.

[21] Appl. No.: 223,884

[22] Filed: Apr. 6, 1994

Related U.S. Application Data

[62] Division of Ser. No. 52,960, Apr. 23, 1993, Pat. No. 5,334,767, which is a division of Ser. No. 927,710, Aug. 10, 1992, Pat. No. 5,239,095, which is a continuation-in-part of Ser. No. 781,039, Oct. 21, 1991, abandoned, which is a continuation-in-part of Ser. No. 748,116, Aug. 21, 1991, abandoned.

[51] Int. Cl.$^6$ .................... C07D 215/227; C07D 215/38
[52] U.S. Cl. .............. 546/101; 560/21; 560/45; 560/47; 560/48; 562/401
[58] Field of Search ................ 546/101; 562/401; 560/21, 45, 47, 48

[56] References Cited

U.S. PATENT DOCUMENTS

| | | | |
|---|---|---|---|
| 4,511,569 | 4/1985 | Smith et al. | 514/290 |
| 4,749,791 | 6/1988 | Aschwanden et al. | 546/101 |
| 5,030,636 | 7/1991 | Imhof et al. | 514/290 |

FOREIGN PATENT DOCUMENTS

| | | |
|---|---|---|
| 127597 | 12/1984 | European Pat. Off. . |
| 2207135 | 1/1989 | United Kingdom . |

OTHER PUBLICATIONS

Bach et al., *J. Med. Chem.*, 23, 812–814 (1980).
Cannon et al., *J. Med. Chem.*, 22, 341–347 (1979).
Cannon et al., *J. Med. Chem.*, 23, 1–5 (1980).
Cannon et al., *J. Med. Chem.*, 19, 987–993 (1976).
Cannon et al., *J. Med. Chem.*, 29, 2529–2534 (1986).
Cannon et al., *J. Med. Chem.*, 27 190–195 (1984).
Wikstrom et al., *J. Med. Chem.*, 25, 925–931 (1982).
Cannon et al., *J. Pharm. Sci.*, 74, 672–675 (1985).
Kiguchi et al., *Heterocycles*, 18, 217–220 (1982).
Ninomiya et al., *J. Chem. Soc., Perkin Trans 1*, 2967–2971 (1983).
Ninomiya et al., *J. Chem. Soc., Perkin Trans 1*, 2911–2917 (1984).
Cannon et al., *Synthesis*, 6, 494–496 (1986).
Horii et al., *Chem. Pharm. Bull.*, 16, 668–671 (1968).
Horii et al., *Chem. Pharm. Bull.*, 14, 1227–1236 (1966).
Costall et al., *J. Pharm. Pharmacol.*, 34, 246–254 (1982).
Horii et al., *Chem. Pharm. Bull.*, 12, 1405–1415 (1964).
Horii et al., *J. Org. Chem.*, 29, 2768–2769 (1964).
Cannon et al., *J. Med. Chem.*, 33 (7), 2000–2006 (1990).
d'Angelo, Jean et al., *Tet Lett.*, 29(35), 4427–4430 (1988).
March, Terry, *Adv. Org. Chem. Reactions, Mech. & Structure*, 3rd ed., p. 1066 (1985).
Chemical Abstracts 78, (1973), 71780A.

*Primary Examiner*—Bernard Dentz
*Assistant Examiner*—D. Margaret M. Mach
*Attorney, Agent, or Firm*—Joseph A. Jones

[57] ABSTRACT

This invention relates to hexa- and octahydrobenzo[f]quinolin-3-ones, pharmaceutical formulations containing those compounds and methods of their use as steroid 5α-reductase inhibitors.

2 Claims, No Drawings

BENZO[F]QUINOLINONES

This application is a divisional of application Ser. No. 08/052,960, filed Apr. 23, 1993, now U.S. Pat. No. 5,334,767; which is a divisional of application Ser. No. 07/927,710, filed Aug. 10, 1992, now U.S. Pat. No. 5,239,095; which is a continuation-in-part of application Ser. No. 07/781,039, filed Oct. 21, 1991, now abandoned; which is a continuation-in-part of application Ser. No. 07/748,116, filed Aug. 21, 1991, now abandoned.

BACKGROUND OF THE INVENTION

The present invention relates to hexa- and octahydrobenzo[f]quinolinones, pharmaceutical formulations containing those compounds and their use as steroid 5α-reductase inhibitors.

It is generally known that certain undesirable physiological conditions such as benign prostatic hyperplasia, male pattern baldness, ache vulgaris, seborrhea, androgenic alopecia, hirsutism and prostatic cancer are androgen mediated conditions dependent on 5α-dihydrotestosterone (DHT).

The enzyme 5α-reductase mediates the conversion of testosterone to the more potent androgen DHT locally, in the target organ. It has been postulated, and demonstrated, that inhibitors of 5α-reductase should block the formation of DHT and bring about amelioration of the above undesirable physiological conditions. Recently, two 5α-reductase isozymes (designated types 1 and 2) have been described in humans, Andersson et al., *Proc. Natl. Acad. Sci. U.S.A.*, 87, 3640–3644 (1990; Andersson et al., *Nature*, 354, 159–161 (1991). In addition to certain structural differences, the two isozymes exhibit some differences with respect to their biochemical properties, expression patterns, genetics, and pharmacology, Andersson et al., *Nature*, 354, 159–161 (1991); Jenkins, et al., *Journal of Clinical Investigation*, 89, 293–300 (1992). Further elucidation of the roles that the two 5α-reductase isozymes play in androgen action is currently the subject of intense research. These isozymes are generally described as 5α-reductase 1 or 2, or type 1 or type 2 5α-reductase.

Compounds reportedly useful for inhibiting 5α-reductase are generally steroid derivatives such as the azasteroids in Rasmusson, etal., *J. Med. Chem.*, 29, (11), 2298–2315 (1986); and benzoylaminophenoxy-butanoic acid derivatives such as those disclosed in EPO 291 245.

Certain benzo[f]quinolinone compounds are known. See, for example, Cannon, et al., *Synthesis*, 6, 494–496 (1986); Kiguchi, et al., *Heterocycles*, 18, (Special Issue), 217–220 (1982); Cannon et al., *J. Med. Chem.*, 22, (4), 341–347 (1979); Cannon, et al., *J. Med. Chem.*, 23 (1), 1–5 (1980); Ninomiya, et al., *J. Med. Chem. Soc. Perkin Trans.* 1, 12, 2911–2917 (1984; and Horri, et al., *Chem, Pharm. Bull.*, 16, (4), 668–671 (1968). These references generally are directed toward the synthesis and dopaminergic evaluation of the compounds disclosed therein. The references do not suggest the novel hexa- and octahydrobenzo[f]quinolinones of the present invention, as defined below, or that such compounds would be expected to have utility as steroid 5α-reductase inhibitors.

Accordingly, it is one object of the present invention to provide novel hexa- and octahydrobenzo[f]quinolinones which are potent selective steroid-5α-reductase inhibitors useful in the treatment of benign prostatic hyperplasia, male pattern baldness, acne vulgaris, seborrhea, androgenic alopecia, hirsutism and prostatic cancer.

A further object of the present invention is to provide therapeutic compositions for treating said conditions.

Still another object is to provide methods for treating said conditions.

Other objects, features and advantages will become apparent to those skilled in the art from the following description and claims.

SUMMARY OF THE INVENTION

The present invention provides novel hexa- and octahydrobenzo[f]quinolin-3-ones which are effective steroid 5α-reductase inhibitors.

More specifically, this invention relates to compounds having the Formula $$\text{I}$$

where

R is hydrogen, $C_1$–$C_4$ alkyl, unsubstituted or substituted phen($C_1$–$C_4$)alkyl;

Z and $Z^1$ are independently selected from hydrogen and $C_1$–$C_4$ alkyl or one of Z and $Z^1$ combines with $R^5$ to form a carbon—carbon bond;

Y is hydrogen or methyl or combines with $R^1$ to form a carbon—carbon bond;

$R^1$ is hydrogen or combines with one of Y or $R^3$ to form a carbon—carbon bond;

$R^2$ is hydrogen or $C_1$–$C_4$ alkyl;

$R^3$ is hydrogen or combines with $R^1$ to form a carbon—carbon bond;

$R^4$ is hydrogen or combines with $R^5$ to form a carbon—carbon-bond;

$R^5$ is hydrogen or combines with one of Z or $Z^1$ to form a carbon—carbon bond;

n is 1 or 2;

X is hydrogen, halogen, $NO_2$, cyano, $CF_3$, $C_1$–$C_6$ alkyl, $C_1$–$C_6$ alkoxy, carboxy, $C_1$–$C_6$ alkoxycarbonyl, amino, $C_1$–$C_4$ alkylamino, $C_1$–$C_4$ dialkylamino, amido, $C_1$–$C_4$ alkylamido, $C_1$–$C_4$ dialkylamido, mercapto, $C_1$–$C_6$ alkylthio, $C_1$–$C_6$ alkylsulfinyl, $C_1$–$C_6$ alkylsulfonyl, or a group —A—$R^6$ where A is $C_1$–$C_6$ alkylene $C_2$–$C_6$ alkenylene or $C_2$–$C_6$ alkynylene; and $R^6$ is halogen, hydroxy, $CF_3$, $C_1$–$C_6$ alkoxy, carboxy, $C_1$–$C_6$ alkoxycarbonyl, amino, $C_1$–$C_4$ alkylamino, $C_1$–$C_4$ dialkylamino, amido, $C_1$–$C_4$ alkylamido, $C_1$–$C_4$ dialkylamido, $C_1$–$C_4$ alkylsulfonylamino, aminosulfonyl or $C_1$–$C_4$ alkylaminosulfonyl, or a pharmaceutically acceptable salt thereof; provided that (a) at least one of $R^1$ and $R^5$ is hydrogen;

(b) when R is hydrogen, methyl, ethyl or benzyl, X is other than hydrogen or methoxy; and (c) when R is methyl, $R^2$ is other than methyl.

This invention also provides pharmaceutical formulations which comprise, a compound of the above Formula I, or a pharmaceutically acceptable salt thereof in association with a pharmaceutically acceptable carrier, diluent, or excipient.

A further embodiment of the present invention is a method for inhibiting 5α-reductase. More particularly, further embodiments are methods for treating a variety of disorders which have been linked to 5α-reductase activity in mammals. Included among those disorders are benign prostatic hyperplasia, male pattern baldness, acne vulgaris, seborrhea, androgenic alopecia, hirsutism and prostatic cancer. These methods employ a compound of Formula I or a pharmaceutically acceptable salt thereof. Although the compounds of the present invention inhibit both 5α-reductase isozymes, said compounds exhibit greater selectivity as type 1 5α-reductase inhibitors.

A further embodiment of this invention is a class of novel intermediates useful in the preparation of compounds of this invention as well as a process for preparing substantially pure optically active compounds of the present invention.

The intermediates have the Formula

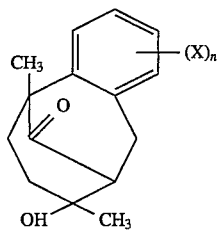

II where
X is hydrogen, halogen, $NO_2$, cyano, $CF_3$, $C_1$–$C_6$ alkyl, $C_1$–$C_6$ alkoxy, carboxy, $C_1$–$C_6$ alkoxycarbonyl, amino, $C_1$–$C_4$ alkylamino, $C_1$–$C_4$ dialkylamino, amido, $C_1$–$C_4$ alkylamido, $C_1$–$C_4$ dialkylamido, mercapto, $C_1$–$C_6$ alkylthio, $C_1$–$C_6$ alkylsulfinyl, $C_1$–$C_6$ alkylsulfonyl, or a group —A—$R^6$ where A is $C_1$–$C_6$ alkylene, $C_2$–$C_6$ alkenylene or $C_2$–$C_6$ alkynylene; and $R^6$ is halogen, hydroxy, $CF_3$, $C_1$–$C_6$ alkoxy, carboxy, $C_1$–$C_6$ alkoxycarbonyl, amino, $C_1$–$C_4$ alkylamino, $C_1$–$C_4$ dialkylamino, amido, $C_1$–$C_4$ alkylamido, $C_1$–$C_4$ dialkylamido, $C_1$–$C_4$ alkylsulfonylamino, aminosulfonyl or $C_1$–$C_4$ alkylaminosulfonyl; and n is 1 or 2; or a pharmaceutically acceptable salt thereof.

The process aspect of this invention which employs the intermediate of Formula II is a process for preparing a substantially pure optically active compound having the Formula

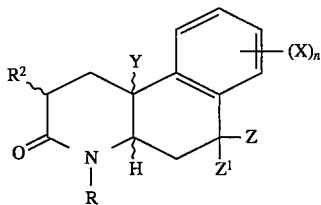

where
R is hydrogen, $C_1$–$C_4$ alkyl, unsubstituted or substituted phen($C_1$–$C_4$)alkyl;

Z and $Z^1$ are independently selected from hydrogen and $C_1$–$C_4$ alkyl;

Y is methyl;

$R^2$ is hydrogen or $C_1$–$C_4$ alkyl;

n is 1 or 2;

X is hydrogen, halogen, $NO_2$, cyano, $CF_3$, $C_1$–$C_6$ alkyl, $C_1$–$C_6$ alkoxy, carboxy, $C_1$–$C_6$ alkoxy-carbonyl, amino, $C_1$–$C_4$ alkylamino, $C_1$–$C_4$ dialkylamino, amido, $C_1$–$C_4$ alkylamido, $C_1$–$C_4$ dialkylamido, mercapto, $C_1$–$C_6$ alkthio, $C_1$–$C_6$ alkylsulfinyl, $C_1$–$C_6$ alkylsulfonyl, or a group —A—$R^6$ where A is $C_1$–$C_6$ alkylene or $C_2$–$C_6$ alkenylene or $C_2$–$C_6$ alkynylene; and $R^6$ is halogen, hydroxy, $CF_3$, $C_1$–$C_6$ alkoxy, carboxy, $C_1$–$C_6$ alkoxycarbonyl, amino, $C_1$–$C_4$ alkylamino, $C_1$–$C_4$ dialkylamino, amido, $C_1$–$C_4$ alkylamido, $C_1$–$C_4$ dialkylamido, $C_1$–$C_4$ alkylsulfonylamino, aminosulfonyl or $C_1$–$C_4$ alkylaminosulfonyl, or a pharmaceutically acceptable salt thereof; which comprises a) reacting a 1-methyl-2-tetralone with an optically active amine to afford a corresponding 1-methylenamine; and b) reacting the 1-methylenamine with an α, β -unsaturated carbonyl compound to afford a corresponding methanobenzocyclooctane -4-one; and c) reacting the methanobenzocyclooctane -4-one with an acidic or basis catalyst to afford a corresponding 2,3,4,4a,9,10-hexahydro-4a-methyl-phenanthren-2-one; and d) oxidatively cleaving said phenanthren-2-one to afford a corresponding 3-[1-methyl-1- (2-keto- 1,2,3,4-tetrahydronaphthyl)]propionic acid; and e) reacting said propionic acid with ammonia or a primary amine to afford a corresponding 10b-methyl- 1,2,3,4,6,10b-hexahydrobenzo[ f]quinolin-3-one; and f) reducing said hexahydrobenzo[f]quinolin- 3-one to afford an octahydrobenzo[f]-quinolin-3-one as defined above.

DETAILED DESCRIPTION OF THE INVENTION

As used herein, the term "alkyl" means a straight or branched alkyl radical having the stated number of carbon atoms. Such alkyl groups include methyl, ethyl, n-propyl, isopropyl, n-butyl, isobutyl, sec-butyl, t-butyl and, where indicated, higher homologs and isomers such as n-pentyl, n-hexyl, 2-methylpentyl and the like.

The term "alkylene" means a bivalent straight chain alkyl radical having the stated number of carbon atoms such as methylene, 1,2-ethanediyl, 1,3-propanediyl, 1,4-butanediyl, 1,5-pentanediyl, 1,6-hexanediyl. Similarly, "alkenylene" means a bivalent unsaturated straight chain hydrocarbon group having the stated number of carbon atoms and a single carbon—carbon double bond such as vinylene, 1 -propene-1,3-diyl, 2-propene-1,3-diyl, 2-butene-1,4-diyl, 1 -butene-1, 4-diyl and the like. Also similarly, "alkynylene" means a bivalent straight chain hydrocarbon group having the stated number of carbon atoms and a single carbon—carbon triple bond such as 1,2-acetylenediyl, 1-propyne-1,3-diyl, 2 -butyne-1,4-diyl the like.

The term "phen($C_1$–$C_4$)alkyl" means a one to four carbon, straight or branched chain, alkyl radical monosubstituted with an unsubstituted or substituted phenyl ring where the substituents are the same or different halogen, $C_1$–$C_4$ alkyl, $C_1$–$C_4$ alkoxy, amino, $C_1$–$C_4$ alkylamino or $C_1$–$C_4$ dialkylamino. Typical phen($C_1$–$C_4$ )alkyl groups include benzyl, 2-pheneth-1-yl, 3-phenprop-1-yl, 4-phenbut-1-yl, 1-pheneth-1-yl, 2-phenprop-1-yl, 2- (4-halophenyl)eth-1-yl, 4-halobenzyl, and the like.

The term "alkoxy" means any of methoxy, ethoxy, n-propoxy, isopropoxy and the like. The term "halogen" and "halo" means any of fluoro, chloro, bromo, and iodo. The term "alkylthio" means any of methylthio, ethylthio, n-propylthio, isopropylthio and the like.

The term "amido" means an aminocarbonyl (—C(O)NH₂) group. The term "alkylamino" means a group —NH(C₁–C₄ alkyl) and the term "alkylamido" means a group —C(O)NH(C₁–C₄ alkyl). Where a "C₁–C₄ dialkylamino" (—N(C₁–C₄ alkyl)₂) or "C₁–C₄ dialkylamido" (—C(O)N(C₁–C₄ alkyl)₂) substituent is indicated, each alkyl group, independently, has one to four carbon atoms.

The term "alkylsulfonyl" means a group —S(O)(alkyl) where the alkyl group has the stated number of carbon atoms. Similarly, the term "alkylsulfonyl" means a group —SO₂(alkyl) where the alkyl group has the stated number of carbon atoms. The term "alkylsulfonylamino" means a group —NHSO₂(C₁–C₄ alkyl). The term "aminosulfonyl" means a group —SO₂NH₂ and the term "alkylaminosulfonyl" means a group —SO₂NH(C₁–C₄ alkyl).

The octahydrobenzo[f]quinolinones of the present invention are those compounds of formula I where $R^1$, $R^3$, $R^4$ and $R^5$ are hydrogen. Correspondingly, the hexahydrobenzo[f] quinolinones of the present invention are those compounds of formula I having two less protons, as described in the definitions for formula I.

The compounds of the present invention possess at least one asymmetric carbon represented by the carbon atom labeled with an asterisk in Formula Ia, below.

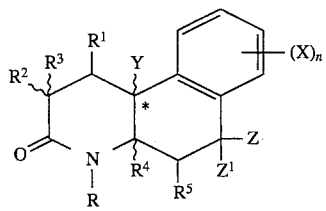

Ia

The compounds of the present invention also exist as individual cis-d and cis-1-stereoisomers as well as trans-d- and trans-1-stereoisomers and mixtures of such isomers. The two cis and two trans configurations are shown below in Formula Ib–Ie.

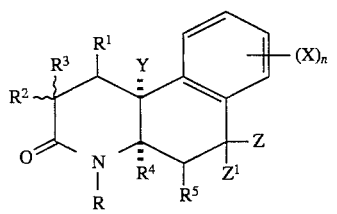

Ib

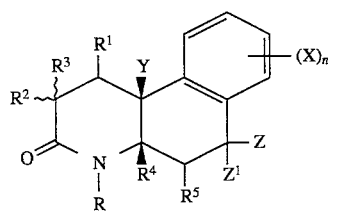

Ic

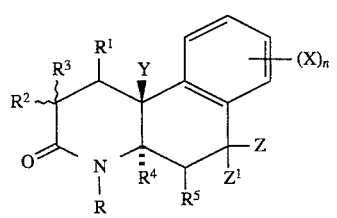

Id

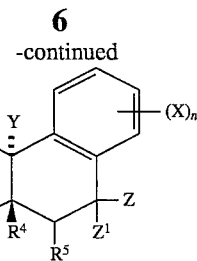

Ie

Accordingly, the compounds of the present invention include not only mixtures of two or more of such individual isomers but also an individual isomer.

In addition, further diastereomers exist depending upon the $R^2$, Z and $Z^1$ substituents. The compounds of the present invention include mixtures of two or more diastereomers, and the individual isomers.

The following compounds illustrate compounds contemplated within the scope of Formula I:

cis-dl-8-bromo-4-methyl-1,2,3,4,4a,5,6,10b-octahydrobenzo[f]quinolin-3-one;

trans-dl-8-bromo-4-methyl-1,2,3,4,4a,5,6,10b-octahydrobenzo[f]quinolin-3-one;

trans-dl-8-bromo-1,2,3,4,4a,5,6,10b-octahydrobenzo-[f]quinolin-3-one;

trans-dl-8-iodo-4-methyl-1,2,3,4,4a,5,6,10b-octahydrobenzo[f]quinolin-3-one;

trans-dl-8,9-dichloro-1,2,3,4,4a,5,6,10b-octahydrobenzo-[f]quinolin-3-one;

trans-dl-8,9-dichloro-4-methyl-1,2,3,4,4a,5,6,10b-octahydrobenzo[f]quinolin-3-one;

trans-dl-8-chloro-4-methyl-1,2,3,4,4a,5,6,10b-octahydrobenzo[f]quinolin-3-one;

cis-dl-8-chloro-4-methyl-1,2,3,4,4a,5,6,10b-octahydrobenzo[f]quinolin-3-one;

trans-dl-4,8-dimethyl-1,2,3,4,4a,5,6,10b-octahydrobenzo[f]quinolin-3-one;

cis-dl-4,8-dimethyl-1,2,3,4,4a,5,6,10b-octahydrobenzo-[f]quinolin-3-one;

trans-dl-8-fluoro-4-methyl-1,2,3,4,4a,5,6,10b-octahydrobenzo[f]quinolin-3-one;

cis-dl-8-fluoro-4-methyl-1,2,3,4,4a,5,6,10b-octahydrobenzo[f]quinolin-3-one;

trans-dl-4-methyl-1,2,3,4,4a,5,6,10b-octahydrobenzo-[f]quinolin-3-one;

cis-dl-4-methyl-1,2,3,4,4a,5,6,10b-octahydrobenzo[f]quinolin-3-one;

cis-dl-1,2,3,4,4a,5,6,10b-octahydrobenzo[f]quinolin-3-one;

trans-dl-8-fluoro-1,2,3,4,4a,5,6,10b-octahydrobenzo-[f]quinolin-3-one;

trans-dl-8-ethoxycarbonylethenediyl-4-methyl-1,2,3,4,4a,5,6,10b-octahydrobenzo[f]quinolin-3-one;

trans-dl-8-chloro-1,2,3,4,4a,5,6,10b-octahydrobenzo-[f]quinolin-3-one;

trans-dl-8-ethoxy-1,2,3,4,4a,5,6,10b-octahydrobenzo-[f]quinolin-3-one;

trans-dl-8-methoxy-4-methyl-1,2,3,4,4a,5,6,10b-octahydrobenzo[f]quinolin-3-one;

trans-dl-8-methyl-1,2,3,4,4a,5,6,10b-octahydrobenzo-[f]quinolin-3-one;

trans-dl-1,2,3,4,4a,5,6,10b-octahydrobenzo[f]quinolin-3-one;

trans-dl-8-ethoxycarbonylethanediyl-4-methyl-1,2,3,4,4a,5,6,10b-octahydrobenzo[f]quinolin-3-one;

trans-dl-8-methoxycarbonylethenediyl-4-methyl-1,2,3,4,4a,5,6,10b-octahydrobenzo[f]quinolin-3-one;

trans-dl-8-carboxyethenediyl-4-methyl-1,2,3,4,4a,5,6,10b-octahydrobenzo[f]quinolin-3-one;

trans-dl-8-t-butylaminocarbonylethenediyl-4-methyl-1,2,3,4,4a,5,6,10b-octahydrobenzo[f]quinolin-3-one;

trans-dl-8-chloro-2-(α-methyl)-4-methyl-1,2,3,4,4a,5,6,10b-octahydrobenzo[f]quinolin-3-one;

trans-dl-8-chloro-2-(β-methyl)-4-methyl-1,2,3,4,4a,5,6,10b-octahydrobenzo[f]quinolin-3-one;

trans-dl-8-bromo-6,6-dimethyl-1,2,3,4,4a,5,6,10b-octahydrobenzo[f]quinolin-3-one;

trans-dl-8-bromo-4,6,6-trimethyl-1,2,3,4,4a,5,6,10b-octahydrobenzo[f]quinolin-3-one;

cis-dl-8-bromo-4,6,6-trimethyl-1,2,3,4,4a,5,6,10b-octahydrobenzo[f]quinolin-3-one;

trans-dl-8-t-butyl1,2,3,4,4a,5,6,10b-octahydrobenzo[f]quinolin-3-one;

trans-dl-8-t-butyl-4-methyl-1,2,3,4,4a,5,6,10b-octahydrobenzo[f]quinolin-3-one;

trans-dl-8-fluoro-4,10b-dimethyl-1,2,3,4,4a,5,6,10b-octahydrobenzo[f]quinolin-3-one;

cis-dl-8-fluoro-4,10b-dimethyl-1,2,3,4,4a,5,6,10b-octahydrobenzo[f]quinolin-3-one;

trans-dl-8-chloro-4,10b-dimethyl-1,2,3,4,4a,5,6,10b-octahydrobenzo[f]quinolin-3-one;

cis-dl-8-chloro-4,10b-dimethyl-1,2,3,4,4a,5,6,10b-octahydrobenzo[f]quinolin-3-one;

trans-dl-10b-methyl-1,2,3,4,4a,5,6,10b-octahydrobenzo[f]quinolin-3-one;

trans-dl-4,10b-dimethyl-1,2,3,4,4a,5,6,10b-octahydrobenzo[f]quinolin-3-one;

trans-dl-8-chloro-10b-methyl-1,2,3,4,4a,5,6,10b-octahydrobenzo[f]quinolin-3-one;

cis-dl-8-chloro-10b-methyl-1,2,3,4,4a,5,6,10b-octahydrobenzo[f]quinolin-3-one;

trans-dl-9-nitro-1,2,3,4,4a,5,6,10b-octahydrobenzo[f]quinolin-3-one;

trans-dl-9-nitro-4-methyl-1,2,3,4,4a,5,6,10b-octahydrobenzo[f]quinolin-3-one;

trans-dl-9-amino-4-methyl-1,2,3,4,4a,5,6,10b-octahydrobenzo[f]quinolin-3-one;

trans-dl-9-chloro-4-methyl-1,2,3,4,4a,5,6,10b-octahydrobenzo[f]quinolin-3-one;

trans-dl-8-chloro-3,4,4a,5,6,10b-hexahydrobenzo[f]quinolin-3-one;

dl-8-chloro-2,3,4,4a,5,6-hexahydrobenzo[f]quinolin-3-one;

trans-dl-8-bromo-4-methyl-3,4,4a,5,6,10b-hexahydrobenzo[f]quinolin-3-one;

trans-dl-8-chloro-4-methyl-3,4,4a,5,6,10b-hexahydrobenzo[f]quinolin-3-one;

dl-8-chloro-4-methyl-2,3,4,4a,5,6-hexahydrobenzo[f]quinolin-3-one;

trans-dl-8-chloro-2-(α-methyl)-4-methyl-1,2,3,4,4a,10b-hexahydrobenzo[f]quinolin-3-one;

trans-dl-8-t-butylaminocarbonylethanediyl-4-methyl-1,2,3,4,4a,5,6,10b-octahydrobenzo[f]quinolin-3-one;

trans-dl-8-phenyl-4-methyl-1,2,3,4,4a,5,6,10b-octahydrobenzo[f]quinolin-3-one;

trans-dl-8-vinyl-4-methyl-1,2,3,4,4a,5,6,10b-octahydrobenzo[f]quinolin-3-one;

trans-dl-8-ethoxycarbonyl-4-methyl-1,2,3,4,4a,5,6,10b-octahydrobenzo[f]quinolin-3-one;

Preferred compounds of the present invention are those of Formula I where:

R is hydrogen or $C_1$–$C_4$ alkyl;

Z and $Z^1$ are independently hydrogen or methyl;

Y is hydrogen or methyl, and is in a trans configuration in relation to the 4a position hydrogen;

$R^1$, $R^3$, $R^4$ and $R^5$ are hydrogen;

$R^2$ is hydrogen or methyl;

n is 1 or 2;

x is halogen, $CF_3$, $C_1$–$C_6$ alkyl, $C_1$–$C_4$ alkoxy or —A—$R_6$ where A is $C_1$–$C_4$ alkylene and $R^6$ is $C_1$–$C_4$ alkoxycarbonyl; or a pharmaceutically acceptable salt thereof; provided that (b) when R is hydrogen, methyl or ethyl, X is other than hydrogen or methoxy; and c) when R is methyl, $R^2$ is other than methyl.

Most preferred compounds of the present invention are those of Formula I where

R is hydrogen or methyl;

Z and $Z^1$ are both hydrogen or methyl;

Y is hydrogen or methyl, and is in a trans configuration in relation to the 4a position hydrogen;

$R^1$, $R^3$, $R^4$ and $R^5$ are hydrogen;

$R^2$ is hydrogen or methyl;

n is 1 or 2;

X is halogen, $CF_3$, or $C_1$–$C_4$ alkyl; or a pharmaceutically acceptable salt thereof; provided that (c) when R is methyl, $R^2$ is other than methyl.

As mentioned above, the invention includes pharmaceutically acceptable salts of the compounds defined by the above formula. Although generally neutral, a particular compound of this invention can possess a sufficiently acidic, a sufficiently basic, or both functional groups, and accordingly react with any of a number of nontoxic inorganic bases, and nontoxic inorganic and organic acids, to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene-sulfonic, methanesulfonic acid, oxalic acid, p-bromo-phenyl-sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4- dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from nontoxic inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate. The potassium and sodium salt forms are particularly preferred.

The compounds of the present invention, or their precursors, are prepared using procedures known to those of ordinary skill in the art. Those compounds of the present invention where Y is hydrogen are preferably synthesized according to the following Scheme 1.

nitromethane, 1,2-dichloroethane, nitrobenzene, and the like, preferably methylene chloride. Activation of phenacetyl chloride with the Lewis acid is carried out at temperatures of from about −78° C. to about 25° C.

Addition of ethylene is exothermic in nature and temperatures from about −78° C. to about 30° C. are generally employed using standard cooling procedures.

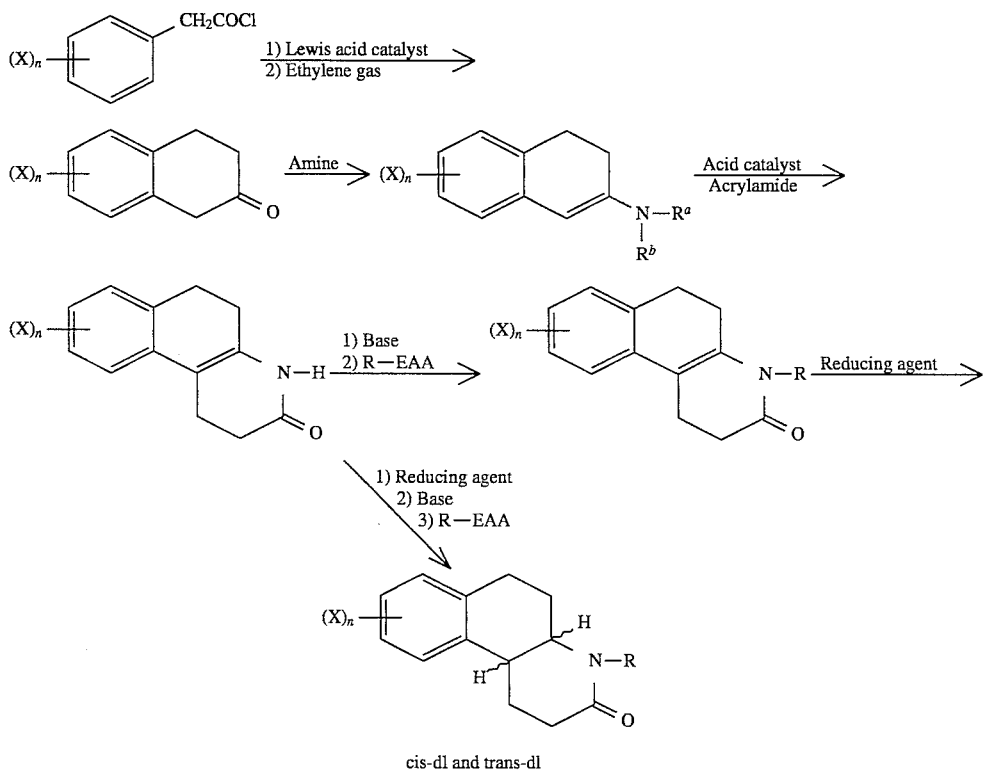

cis-dl and trans-dl

Where X, n, and R are as defined above for Formula I, R-EAA is an electrophilic alkylating agent, and $R^a$ and $R^b$ are independently selected from hydrogen and $C_1$-$C_4$ alkyl, or may be taken together with the nitrogen atom to afford a 5–7 membered heterocyclic group which may also include an oxygen atom, provided that both $R^a$ and $R^b$ cannot be hydrogen at the same time.

As depicted in Synthetic Scheme 1, the $\Delta4_a$-$10_b$ hexahydrobenzo[f]quinolinones represent the intermediates which, upon reduction of the double bond, affords compounds of this invention and/or compounds useful as intermediates for the preparation of compounds of this invention.

The hexahydrobenzo[f]quinolinones are prepared from an unsubstituted or appropriately ring-substituted phenacetyl chloride. The phenacetyl chloride is commercially available or is prepared by procedures well-known to those skilled in the art. Typically, suitably substituted phenylacetic acid is reacted with thionyl chloride, phosphorous trichloride, oxalyl chloride, or phosphorous pentachloride, preferably thionyl chloride, under conditions known to those skilled in the art, to afford the corresponding phenacetyl chloride.

By a Friedel-Crafts acylation reaction of the phenacetyl chloride with ethylene in the presence of a Lewis acid catalyst and in an inert or substantially inert solvent or mixture of solvents, ring closure is effected to afford a 2-tetralone. Suitable Lewis acid catalysts include $AlBr_3$, $AlCl_3$, $GaCl_3$, $FeCl_3$, $SbCl_5$, $ZrCl_4$, $SnCl_4$, $BCl_3$, $BF_3$, $SbCl_3$, and the like, preferably $AlCl_3$. Solvents useful for this reaction include carbon disulfide, methylene chloride, The 2-tetralone reaction product is then aminated with a primary or secondary amine, preferably pyrrolidine, in an inert or substantially inert solvent or mixture of solvents to afford the corresponding enamine. In the case of a primary amine, this may be accompanied by the imine tautomer. The reaction is driven to completion by the removal of water which may be accomplished at elevated temperatures of from about 80°–110° C. using a suitable solvent azeotrope or at about room temperature through the use of a suitable dehydrating agent such as molecular sieves or magnesium sulfate. Suitable solvents are aprotic organic solvents such as benzene, toluene, THF, $CH_2Cl_2$ and ethyl acetate.

The enamine reaction product is then reacted with acrylamide in the presence of an acid and in the presence or absence of an inert or substantially inert solvent or mixture of solvents to afford a hexahydro-2-(1H)-benzo[f]quinolinone. Acids useful in this reaction include strong organic or mineral acids, preferably p-toluene sulfonic acid (pTSA). Although the reaction can be carried out in a solvent, preferably no solvent is used. The reaction is carried out at temperatures of from about 90° C. to about 130° C.

The hexahydro-2(1H)-benzo[f]quinolinone may then be reduced to the corresponding octahydrobenzo[f]quinolinones of the present invention. The octahydrobenzo[f]quinolines may then be N-alkylated to afford further compounds of the present invention.

Alternatively, the hexahydro-2(1H)-benzo[f]quinolinones may first be N-alkylated and then reduced to the corresponding N-alkyl-octahydrobenzo[f]quinolin-(3)-ones of the present invention.

Reduction is carried out by reacting the hexahydrobenzo[f]quinolinone or N-alkyl-hexahydrobenzo[f]quinolinone with an appropriate reducing agent in an inert or substantially inert solvent or mixture of solvents. Suitable reducing agents include hydrogenation over a metal catalyst, and hydride transfer reagents such as ammonium formate over a metal catalyst, preferably triethylsilane/trifluoroacetic acid. Useful solvents include inert or substantially inert organic solvents, preferably methylene chloride. Temperatures of from about 0° C. to about 60° C. are employed, preferably at about 25° C.

The N-alkylation is carried out by reacting the hexahydrobenzo[f]quinolinone or octahydrobenzo[f]quinolinone with an electrophilic alkylating agent, R-EAA where R is as defined above for Formula I, in the presence of a base, in an inert or substantially inert solvent or mixture of solvents. For this reaction, EAA is preferably iodo. The base is generally a metal hydride, metal amide or metal alkoxide, preferably sodium hydride. Generally, this reaction is carried out at temperatures of from about −30° C. to about solvent reflux.

Those compounds of the present invention where Y is methyl are preferably synthesized according to the following Scheme 2.

present invention and/or compounds useful as intermediates for the preparation of compounds of this invention.

An enamine is prepared by the procedures depicted in Schemes 1 and 2 and described above for Synthetic Scheme 1. The enamine is alkylated by reaction with an electrophic alkylating agent, preferably methyl iodide, in an inert or substantially inert solvent or mixture of solvents. Temperatures for this reaction are generally from about 0° C. to about 60° C. The reaction mixture is then subjected to hydrolysis with aqueous acid, preferably a mixture of sodium acetate, ethyl acetate and acetic acid. Temperatures of from about 0° C. to about 30° C. are employed in this reaction to afford a 1-methyl-2-tetralone.

The 1-methyl-2-tetralone is then further reacted as depicted in Scheme 2 using the reagents and procedures described above for Scheme 1, to afford the compounds of the present invention where Y is methyl.

Those compounds of the present invention where Z, $Z^1$, or both, are $C_1$–$C_4$ alkyl are prepared substantially according to the procedures in Scheme 1 and Scheme 2 except that during the Friedel-Crafts ring closure reaction of phenacetyl chloride, an appropriate alkene, is used, rather than the ethylene shown in both Schemes 1 and 2. Examples of suitable alkenes for use in this reaction include propylene, 1-butene, 2-butene, isobutylene, 3,3-dimethyl-1-butene, 2-pentene, 4-methyl-2-pentene, 3-methyl-1-butene, 2-methyl-2-butene, 2,3-di-methyl-2-butene and the like.

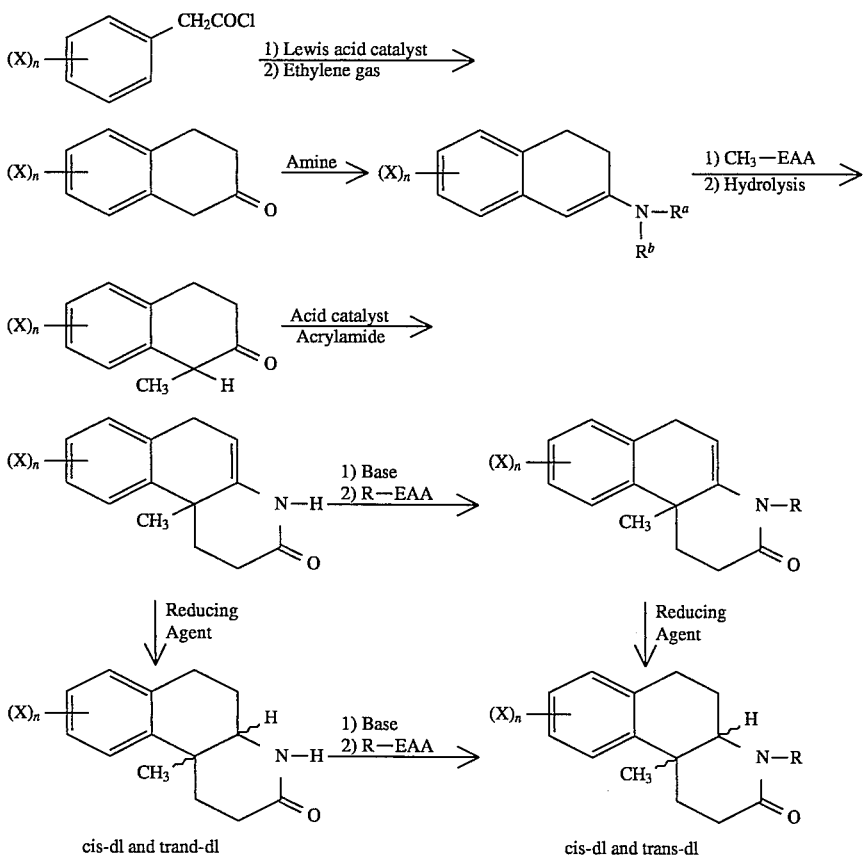

where X, n, and R as defined above for Formula I, and $R^a$, $R^b$ and R-EAA are as defined above for Scheme 1.

As depicted above in Synthetic Scheme 2, the 4a-methyl-hexahydrobenzo[f]quinolin-2(1H)-one are the intermediates which are reduced to afford the compounds of the Those compounds of Formula I where $R^2$ is $C_1$–$C_4$ alkyl are prepared from the compounds afforded by Schemes 1 and 2, preferably where R is $C_1$–$C_4$ alkyl, unsubstituted or substituted phen($C_1$–$C_4$)alkyl as shown in the following reaction Scheme 3:

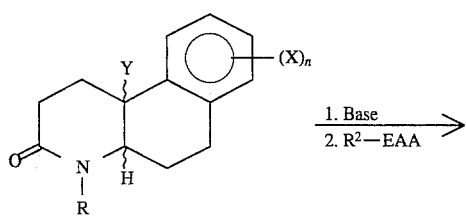

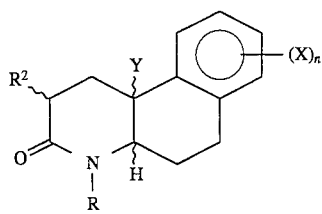

where Y, x, n, R, and R² are as defined above for Formula I except R is not hydrogen, and R²-EAA is an electrophilic alkylating agent where R2 is as defined above for Scheme 1. The R-(alkyl or phenalkyl) compound is reacted with a base, such as a metal amide or metal alkoxide, preferably potassium hexamethyldisilazide, in an inert or substantially inert solvent or mixture of solvents at a temperature of from about −78° C. to about 25° C. Alkylation is then effected by the addition of an appropriate electrophilic alkylating agent, preferably $C_1$–$C_4$ alkyl iodide, to afford the 2-($C_1$–$C_4$ alkyl) compounds of Formula I.

For those compounds of Formula I where R is H, the 4-position nitrogen atom is first blocked with a suitable amino protecting group such as t-butoxycarbonyl or benzyloxycarbonyl and then reacted as shown above in Scheme 3. After alkylating at the 2-position, the 4-position nitrogen atom is deprotected. The protection and deprotection reactions are carried out under standard conditions for such reactions.

An alternative method for preparing those compounds of the present invention where Y is methyl is shown below in Scheme 4.

Scheme 4

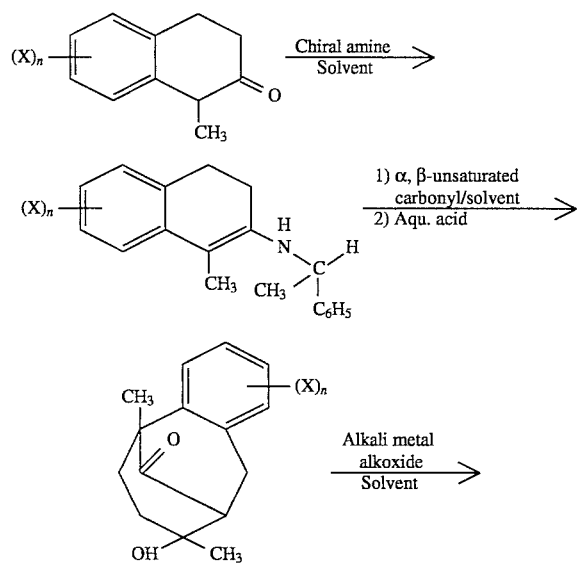

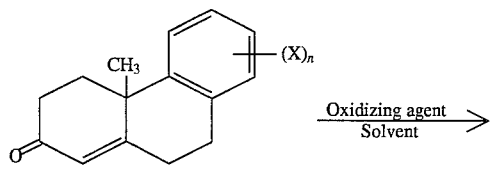

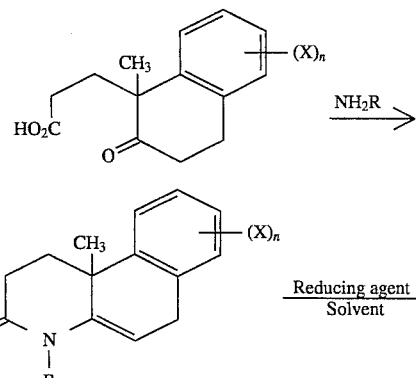

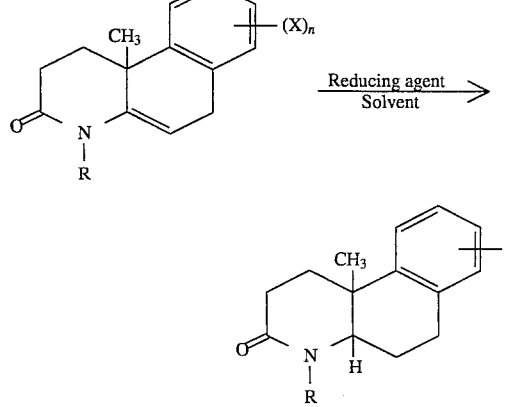

where R, X and n are as defined above for Formula I.

Another aspect of this invention pertains to a particular method for producing optically active isomers of the compounds of this invention. As depicted above in Scheme 4, a 1-methyl-2-tetralone is reacted with a chiral amine, such as preferably 1-phenylethylamine in an inert or substantially inert solvent or mixture of solvents to afford the corresponding enamine. If a primary chiral amine is used, the enamine may be afforded by way of the imine tautomer. The reaction is driven by the removal of water which may be accomplished at elevated temperatures of from about 80° C. to about 110° C. using a suitable solvent azeotrope or at about room temperature through the use of a suitable dehydrating agent such as molecular sieves or magnesium sulfate.

The enamine is then reacted with a suitable alpha, beta-unsaturated carbonyl compound preferably methylvinyl ketone in a Michael addition reaction, followed by hydrolysis with a mild aqueous acid to afford a 5,6,7,8,9,10-hexahydro- 8-hydroxy-5,8-dimethyl-5,9-methanobenzocyclooctan-11-one. This reaction is carried out in an ethereal solvent such as tetrahydrofuran (THF), dioxane or the like under an inert atmosphere, such as argon or nitrogen, at a temperature of from about 10° C. to about 50° C., preferably at about room temperature. Generally, from about stoichiometric amounts of reactants to an excess of the alpha, beta-unsaturated carbonyl compound are employed in this reaction, and preferably an excess of the alpha, beta-unsaturated carbonyl reactant. Suitable acids include organic carboxylic acids and perchloric acid and preferably acetic acid.

The methanobenzocyclooctan-11-one is treated with an acidic or basic catalyst, preferably sodium or potassium ethoxide, in a protic solvent, preferably ethanol, at reflux to afford a 2,3,4,4a,9,10-hexahydro-4a-methyl-phenanthren-2-one.

The phenanthren-2-one is oxidatively cleaved with a suitable oxidizing agent such as ozone, $KMnO_4$, $CrO_3$ or $RuO_4$, preferably Ruthenium tetraoxide, in an inert or substantially inert solvent or mixture of solvents at from about −78° C. to about 100° C., preferably at from about −10° C. to about 10° C. to afford a b-[1-methyl-1-(2-oxo-1,2,3,4-tetrahydronaphthyl)] propionic acid. Generally, the solvent will be an inert solvent or mixture of solvents and preferably the solvent will be a mixture of 2 parts carbon tetrachloride, 3 parts acetonitrile and 2 parts water.

The propionic acid is reacted with ammonia or a primary amine (NH R where R is as defined above for Formula I) in an inert or substantially inert solvent or mixture of solvents preferably 2-propanol, at a temperature of from about 95° C. to about 200° C., preferably from about 165° C. to about 180° C. to afford a 10b-methyl-1,2,3,4,6,10b-hexahydrobenzo[f]quinolin-3-one of the present invention. Preferably this reaction is carried out in the relative absence of oxidizing agents, such as air in, for example, a sealed reactor or the like.

The hexahydrobenzo[f]quinolinone may be reduced to the corresponding octahydro compound of the present invention by substantially the same procedures described above in Schemes 1 and 2.

By following the procedures depicted in Scheme 4 and as described above, the substantially pure optically active isomers of the compounds of this invention where Y is methyl are afforded.

The preferred asymmetric synthesis of the individual enantiomer compounds of Formula I, or their precursors, is carried out by reacting an enamine of the formula Scheme 5:

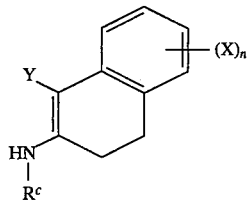

with an acryloyl derivative of the formula

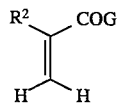

where Y, X, $R^2$ and n are as defined above for Formula I; G is a leaving group such as chlorine, bromine, fluorine, iodine, toluene sulfonate, methane sulfonate and symmetrical or unsymmetrical anhydrides; and $R^c$ is 1-phenethyl. The 1-phenethyl substituent is subsequently cleaved using trifluoroacetic acid. It will be appreciated that the —COG radical of the acryloyl derivative is an activated form of —COOH, which can be activated in other ways such as active esters, mixed anhydrides and the like.

The process conditions for carrying out the preferred individual isomer synthesis of Schemes 4 and 5 are extremely mild. In most instances, it will be found that excellent yields are obtained in short periods of time at temperatures in the range of ambient. For example, temperatures from about 0° to about 150° are used, and reaction times in the range of from about a few minutes to, at maximum, a few hours, are sufficient. The reaction medium is preferably a biphasic mixture of a convenient organic solvent and an aqueous solution of a mild base. Useful solvents include, for example, haloalkanes, ethers including tetrahydrofuran, and nitriles including acetonitrile. Preferred mild bases are alkali metal carbonates and bicarbonates; more highly basic reagents such as alkali and alkaline earth metal hydroxides and the like may be used in some cases, but the bicarbonates are typically preferred. The process may also be performed without a base if desired.

The products of this synthesis are readily isolated by conventional process steps. The use of this process provides a particularly clean synthesis of single-isomer forms of the reaction product.

It will be understood that the products of the present process may be used as such to take advantage of their biological activity, or they may be used as intermediates in additional processes to prepare active compounds within the scope of Formula I.

Those hexahydrobenzo[f]quinolin-3-ones of Formula I having a $\Delta^1$ or $\Delta^5$ carbon—carbon double bond are prepared from the corresponding octahydrobenzo[f]quinolin-3-ones by addition/elimination reactions. The octahydrobenzo[f]quinolin-3-one is reacted with a sulfur or seleno electrophile in the presence of a base, in an aprotic solvent. The base is generally a metal hydride or metal amide, preferably a metal hydride such as sodium hydride. Although generally one equivalent of base is added for each equivalent of octahydrobenzo[f]quinoline, for those compounds where R is hydrogen, a second equivalent of base is added. Temperatures for this reaction are from about 20° C. to about the reflux temperature of the solvent. The addition reactant is a sulfur or seleno electrophile and is carried out at a temperature of from about −50° C. to about −100° C. Suitable sulfur electrophiles are substantially similar to sulfur groups useful in nucelophilic substitution and are known to those skilled in the art, Fatal, "The Chemistry of the Thiol Group," Wiley, New York (1974); Reid, "Organic Chemistry of Bivalent Sulfur", Chemical Publishing Company, New York (1958, 1963); Kharasch, "Organic Sulfur Compounds," Perganon, New York (1961).

Suitable seleno compounds include phenylselenenyl chloride, phenylselenenyl bromide, N-(phenylseleno)phthalimide, diphenyl diselenide, benzeneseleninic anhydride and selenoxides. Specific conditions for a particular seleno reactant are well known or readily ascertained by one skilled in the art, Clive, *Tetrahedron*, 34, 1049–1132 (1978); *Aldrichimica Acta*, 11, 43– 49 (1978); and Miyoshi, et al., *Tetrahedron Lett.*, 23, 4813 (1982).

The elimination reaction is generally carried out under oxidative conditions in an aprotic solvent. March, "Advanced Organic Chemistry", 3rd Ed., p. 912–914, Wiley-Interscience, New York (1985).

The $\Delta^{10b}$ compounds of the present invention are obtained by rearrangement (isomerization) from the corresponding $\Delta^1$ compounds when Y is hydrogen. This reaction is carried out in an aprotic solvent in the presence of an acid or base catalyst, under conditions well known or readily ascertained by one skilled in the art.

The $\Delta^{4a}$ compounds of the present invention are prepared as intermediates by the procedures described above in Scheme 4 and are isolated, rather than reduced to the corresponding octahydrobenzo[f]quinolin-3-one.

The optically active isomers of the racemates of the invention are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization.

Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

A further aspect of the present invention and the preferred method of resolving racemates of those compounds of Formula I where R is hydrogen or $C_1-C_4$ alkyl; Z and $Z^1$ are independently selected from hydrogen and $C_1-C_4$ alkyl; Y is hydrogen; $R^1$, $R^2$, $R^3$, $R^4$ and $R^5$ are all hydrogen; n is 1 or 2; and x is hydrogen, halogen, $NO_2$, $CF_3$, $C_1-C_6$ alkyl, $C_1-C_4$ alkoxy, amino, $C_1-C_4$ alkylamino, $C_1-C_4$ dialkylamino, mercapto, or $C_1-C_6$ alkylthio;

into their component optical isomers comprising essentially the steps of:

(a) contacting a methanol solution of a racemate with a strong acid to afford a 1-(2-methoxycarbonylethyl)-2-(amino)-1,2,3,4-tetrahydronaphthalene;

(b) contacting said tetrahydronaphthalene from (a) with a methanol solution of an optically active di-p-toluoyltartaric acid to afford a corresponding tetrahydronaphthalene salt; and (c) treating said salt from (b) with a base to afford an optically active isomer.

As a further aspect of the present invention, in addition to the process for resolving a racemic mixture of those compounds of formula I specified above, there is provided the di-p-toluoyl-(D)- and (L-)tartaric acid salts of 1-(2-methoxycarbonylethyl)-2-(amino or $C_1-C_4$ alkylamino)- 1,2,3,4-tetrahydronaphthalene.

This resolution is accomplished by dissolving a racemic mixture of optically active isomers as defined above in methanol, and contacting said solution with a strong acid to afford a 1-(2-methoxycarbonylethyl)-2-(amino or $C_1-C_4$ alkylamino)-1,2,3,4-tetrahydronaphthalene intermediate. Suitable strong acids include inorganic acids such as hydrochloric acid, nitric acid, phosphoric acid, sulfuric acid, hydrobromic acid, hydroiodic acid and the like, as well as organic acids, such as aromatic sulfonic acids and the like. Inorganic acids are preferred and sulfuric acid is most preferred. The tetrahydronaphthalene intermediate is then contacted with a methanol solution of an optically active di-p-toluoyltartaric acid to afford a corresponding tetrahydronaphthalene salt. Where the (+) enantiomer is desired, (−)-di-p-toluoyl-L-tartaric acid is used. Correspondingly, where the (−) isomer is desired (+)-di-p-toluoyl-D-tartaric acid is used.

The salt formed can be separated from the mixture by conventional methods. For example, the separated salt can be treated in an aqueous medium with a base to form the free amine which can be extracted from the aqueous phase with a water immiscible solvent. The free amine may be heated to from about 35° C. to about 120° C. to recyclize and afford the desired octahydrobenzo[f]quinolinone, depending upon the extracting solvent used.

Suitable bases for use in the above process are generally weak bases, preferably sodium or potassium carbonate or bicarbonate and most preferably sodium bicarbonate. Suitable water immiscible solvents include methylene chloride, toluene, ethyl acetate, methyl tert-butyl ether, and diethyl ether, preferably methylene chloride.

One skilled in the art will appreciate that the selective crystallization of one diastereomer from an organic solution is also affected by concentration. A relatively low concentration provides pure diastereomer of generally higher purity but lower yield, while the utilization of a higher concentration of racemate and resolving agent will normally provide higher yields of solid, many times at the expense of optical purity.

The compounds employed as initial starting materials in the synthesis of the compounds of this invention are well known and, to the extent not commercially available, are readily synthesized by standard procedures commonly employed by those of ordinary skill in the art.

The pharmaceutically acceptable salts of the invention are typically formed by reacting an octahydrobenzo[f]quinolinone of this invention which possesses suitable acidic or basic functionality with an equimolar or excess amount of acid or base. The reactants are generally combined in a mutual solvent such as diethyl ether or benzene, for acid addition salts, or water or alcohols for base addition salts, and the salt normally precipitates out of solution within about one hour to 10 days, and can be isolated by filtration or other conventional means.

In addition, some of the compounds of the present invention may form solvates with water or common organic solvents. Such solvates are included as compounds of this invention.

The following Examples further illustrate the compounds of the present invention and methods for their synthesis. The Examples are not intended to be limiting to the scope of the invention in any respect and should not be so construed.

EXAMPLE 1

Preparation of cis-dl and trans-dl 8-bromo-4-methyl-1,2,3,4,4a,5,6,10b-octahydrobenzo[f]quinolin-3-one.

A. 4-bromophenylacetyl chloride.

To a 250 ml round bottom flask fitted with a magnetic stirrer was added 4-bromophenylacetic acid (100.0 g; 0.465 mol) and 100 ml of thionyl chloride (163.1 g; 1.37 mol). The resulting slurry was stirred at room temperature for 22.5 hrs. The excess thionyl chloride was evaporated under vacuum to afford 108.5 g of the subtitle compound as a brown liquid.

B. 6-bromo-2-tetralone.

To a cold (−78° C.; dry ice/isopropanol bath) suspension of $AlC_{13}$ (125 g; 0.94 mol) in 1,400 ml $CH_2Cl_2$ was added the acid chloride afforded in Step A (108.5 g; 0.47 mol) dissolved in 400 ml of dry $CH_2Cl_2$ with stirring over one hour. The dry ice/isopropanol bath was removed and the solution was allowed to warm to −10° C. Ethylene was then bubbled into the flask with vigorous stirring. The reaction warmed exothermically to 20° C. at which time the addition of ethylene was stopped. The mixture was stirred at room temperature for three hours, then it was cooled to 0° C. and ice added until no further exotherm was observed. The reaction mixture was diluted with 1 L of ice cold water and stirred until all solids dissolved. The resulting layers were separated and the organic layer washed twice with one liter portions of 1N HCl and then once with 1 L of saturated $Na_2HCO_4$. The organic layer was dried over $Na_2SO_4$ and concentrated under a vacuum to afford a pale yellow crystalline solid.

The 6-bromo-2-tetralone crystals were taken up in a minimum amount of ether. Hexane was cautiously added until the solution just started to turn cloudy. The mixture was refrigerated for four hours, filtered, and washed with cold hexanes to afford 75.6 g of the subtitle compound as a pale yellow crystalline solid (71% yield) melting point 71°–73° C.

C. 2-pyrrolidinyl-6-bromo-3,4-dihydronaphthalene.

To a 250 ml round bottomed flask was added 5.00 g (22.21 mmol) of the 6-bromotetralone afforded above in Step B; 70 ml of dry toluene and 3.1 g (3.7 ml) of pyrrolidine. The flask was equipped with a Dean-Stark trap, a condenser, a nitrogen inlet tube and a magnetic stirrer and the reaction refluxed for four hours. The solvent was evaporated under vacuum to afford 6.02 g (97.4%) of the subtitle compound as a brown crystalline material which was used without further purification.

D. 8-bromo-1,2,3,4,5,6-hexahydrobenzo[f]quinolin-3-one.

The enamine (2.15 g; 7.73 mmol) from Step C, acrylamide (1.10 g; 15.46 mmol) and 100 mg of p-toluene sulfonic acid (pTSA) were mixed thoroughly in a mortar and pestle. The mixture was transferred to a 250 ml round bottomed flask equipped with a magnetic stirrer and nitrogen inlet. Using a mineral oil bath, the mixture was heated to 89° C. at which point the stirred mixture turned black and melted. The temperature was held constant at 89° C. for 1.5 hours. At this point the temperature was increased to 130° C. and was held there for 0.5 hours. The oil bath was removed and 60 ml of water was cautiously added. The resulting murky gray material was mixed thoroughly with a spatula and 80 ml of water was added to aid in filtration. Brown crystals (1.02 grams) were afforded by the filtration. The crystals were taken up in $CHCl_3$ and activated carbon was added. This mixture was stirred for 15 minutes, filtered, and evaporated under vacuum. The residue was taken up in a minimum amount of ethyl acetate with the help of a steam bath, and transferred to an Erlenmeyer flask, equipped with a magnetic stirring bar and sub-merged in a dry ice/acetone bath with stirring to afford the subtitle compound as a white crystalline solid (melting point 215–217 decomp.). 1st crop 940 mg; 2nd crop 175 mg (55% yield).

E. 8-bromo-4-methyl-1,2,3,4,5,6-hexahydrobenzo[f]quinolinone-3-one.

By substantially following the procedures described above 5.17 g of the 8-bromo-1,2,3,4,5,6-hexahydrobenzo[f]quinolin-3-one was obtained. The hexahydrobenzoquinolinone (5.17 g; 19.6 mmol) was dissolved in 60 ml of dry diethyl ether in a 250 ml round bottomed flask. To the solution was added 1.2 g of sodium hydride (60% dispersion in mineral oil). The flask was fitted to a reflux condenser with a stirring bar and the mixture refluxed for 2 hours. The mixture was then cooled to room temperature and 7.35 ml of methyl iodide was added. After addition, the reaction mixture was refluxed for an additional 3 hours. After cooling, the reaction mixture was quenched by the cautious addition of 5 ml of water. The mixture was then concentrated under vacuum affording a pale solid crystals which was taken up in a ethyl acetate/water mixture and the resulting layers separated. The organic layer was washed twice with water and once with brine and then dried over $MgSO_4$ and evaporated under vacuum to afford 5.22 g of a yellow crystalline solid. The solid was recrystallized from acetone to afford 3.55 g (62%) of the subtitle compound as a pale yellow solid. Melting point 126°–128° C.

F. 8-bromo-4-methyl-1,2,3,4,4a,5,6,10b-octahydrobenzo[f]quinolin-3-one.

To a solution of the hexahydrobenzoquinolinone prepared above in Step E (1.17 g; 4.0 mmol) in 10 ml of dry dichloromethane was added triethylsilane (1.37 g; 11.8 mmol). The resulting mixture was stirred for 10 minutes at room temperature. The reaction mixture was cooled in an ice bath and trifluoroacetic acid (5 ml) was added. The resulting mixture was stirred at room temperature for four days. The reaction mixture was concentrated under vacuum. The oil residue was taken up in $CH_2Cl_2$ and washed with saturated $NaHCO_3$. The organic layer was dried over sodium sulfate and concentrated under vacuum to afford an orange oil. Flash chromatography on $SiO_2$ (elution with 0.5% methanol/$CH_2Cl_2$) gave 1.14 g of a light brown oil. Proton NMR spectroscopy revealed the ratio of trans:cis to be 3.2:1.

G. Cis-dl and trans-dl-8-bromo-4-methyl- 1,2,3,4,4a,5,6,10b-octahydrobenzo[f]quinolin-3-one.

The cis and trans isomers were separated by HPLC on $SiO_2$ (in hexane with increasing gradient of ethyl acetate). The trans isomer (Example 1A) came off first affording 631 mg; and the cis (Example 1B) isomer came off second affording 192 mg. The trans isomer was recrystallized from diethyl ether/hexanes to afford 176 mg; melting point 103°–104.5° C.

|  | Elemental Analysis: | | |
| --- | --- | --- | --- |
|  | C | H | N |
| Trans (1A) | | | |
| Calculated: | 57.16 | 5.48 | 4.76 |
| Found: | 57.57 | 5.53 | 4.64 |
| Cis (1B) | | | |
| Calculated: | 57.16 | 5.48 | 4.76 |
| Found: | 57.46 | 5.67 | 4.59 |

EXAMPLE 2

Preparation of trans-dl- 8-bromo- 1,2,3,4,4a,5,6,10b-octahydrobenzo[f]quinolin-3-one.

The compound 8-bromo-1,2,3,4,5,6-hexahydrobenzo[f]-quinolin-3-one was prepared according to the procedures described in Example 1, Steps A, B, C, and D.

The title compound was prepared according to the procedure described above in Example 1, Step F, to afford 84 mg of a white, crystalline material (29% yield) following recrystallization from ethyl acetate; melting point of 252°–254° C. decomp.

|  | Elemental Analysis: | | |
| --- | --- | --- | --- |
|  | C | H | N |
| Calculated: | 55.73 | 5.04 | 5.00 |
| Found: | 55.47 | 5.07 | 4.89 |

EXAMPLE 3

Preparation of trans-dl-8-iodo-4-methyl- 1,2,3,4,4a,5,6,10b-octahydrobenzo[f]-quinolin-3-one.

The compound trans-dl-8-bromo-4-methyl- 1,2,3,4,4a,5,6,10b-octahydrobenzo[f]quinolin- 3-one was prepared according to the procedures described in Example 1, Steps A, B, C, D, E, F, and G.

To a stirred solution of the trans isomer (475 mg; 1.614 mmol) in 3.5 ml of dry dioxane was added hexamethylditin and 54 mg (3 mol %) of tetrakis(triphenylphosphine)palladium. The reaction mixture was refluxed for 2.5 hours, cooled to room temperature, filtered through diatomaceous earth (Celite®) and concentrated to afford a pale yellow oil. The material was further concentrated under a high vacuum overnight at room temperature to afford 677 mg of the corresponding 8-trimethyltin compound as a pale yellow oil which was used below without further purification.

To a cold (−78° C.) solution of the 8-trimethyltin compound prepared above in 5.0 ml CH$_2$Cl$_2$ was added 1.6 ml of 1.0M iodine monochloride dropwise. The reaction mixture was allowed to warm to room temperature over 1.5 hours. The mixture was quenched with 1 ml of water, filtered, and the volatiles evaporated under vacuum to afford a black oily material. The black oily material was flash chromatographed on SiO$_2$ (eluted with 5% isopropanol/ CH$_2$Cl$_2$) to afford a yellow crystalline substance, which was recrystallized from ethyl acetate/hexanes to afford the title compound 141 mg (86% yield) as an off-white crystalline material; melting point: 103°–104.5° C.

| | Elemental Analysis: | | |
|---|---|---|---|
| | C | H | N |
| Calculated: | 49.28 | 4.73 | 4.11 |
| Found: | 49.48 | 4.72 | 3.96 |

EXAMPLE 4

Preparation of trans-dl-8,9-dichloro- 1,2,3,4,4a,5,6,10b-octahydrobenzo[f]quinolin-3-one.

The title compound was prepared employing 3,4-dichlorophenylacetic acid as the starting material according to the procedures described above in Example 1, Steps A, B, C, D, and F, to afford 567 mg of the title compound as an off-white highly crystalline material. Melting point 267°– 268° C. decomp.

| | Elemental Analysis: | | |
|---|---|---|---|
| | C | H | N |
| Calculated: | 57.80 | 4.85 | 5.18 |
| Found: | 58.22 | 5.04 | 5.18 |

EXAMPLE 5

Preparation of trans-dl-8,9-dichloro-4-methyl- 1,2,3,4,4a,5,6,10b-octahydrobenzo[f]quinolin-3-one.

Following the procedures described above in Example 1, Steps A, B, C, D, and F, followed by recrystallization from ethyl acetate trans-dl-8,9-di-chloro-1,2,3,4,4a,5,6,10b-octahydrobenzo[ f]quinolin-3-one was prepared using 3,4-dichlorophenylacetic acid as the starting material.

The title compound was prepared from trans-dl-8,9-dichlorooctahydrobenzo[ f]quinolinone according to the procedures described in Example 1, Step E to afford 117 mg (35% yield) of a beige solid material. Melting point 168°–169° C.

| | Elemental Analysis: | | |
|---|---|---|---|
| | C | H | N |
| Calculated: | 59.17 | 5.32 | 4.93 |
| Found: | 59.45 | 5.08 | 4.83 |

EXAMPLE 6

Preparation of trans-dl-8-chloro-4-methyl- 1,2,3,4,4a,5,6,10b-octahydrobenzo[f]quinolin-3-one.

The title compound, along with the cis-dl-isomer (Example 7), was prepared according to the procedures described in Example 1, Steps A, B, C, D, E, and F using p-chlorophenylacetic acid as the starting material. Separation according to Example 1, Step G, afford 500 mg of the title compound. Melting point 82° C.

| | Elemental Analysis: | | |
|---|---|---|---|
| | C | H | N |
| Calculated: | 67.33 | 6.46 | 5.61 |
| Found: | 67.60 | 6.63 | 5.67 |

EXAMPLE 7

Preparation of cis-dl-8-chloro-4-methyl- 1,2,3,4,4a,5,6,10b-octahydrobenzo[f]quinolin-3-one.

The title compound along with the trans-dl- isomer (Example 6), was prepared according to the procedures described in Example 1, Steps A, B, C, D, E, and F using p-chlorophenylacetic acid as the starting material. Separation according to Example 1, Step G, afforded 200 mg of the title compound as an oil.

| | Elemental Analysis: | | |
|---|---|---|---|
| | C | H | N |
| Calculated: | 67.33 | 6.46 | 5.61 |
| Found: | 67.57 | 6.82 | 5.70 |

EXAMPLE 8

Preparation of trans-dl-4,8-dimethyl- 1,2,3,4,4a,5,6,10b-octahydrobenzo[f]quinolin-3-one.

The title compound along with the cis-dl-isomer (Example 9), was prepared according to the procedures described in Example 1, Steps A, B, C, D, E, and F using p-tolylacetic acid as the starting material. Separation according to Example 1, Step G, afforded 400 mg of the title compound. Melting point 115°–116° C.

| | Elemental Analysis: | | |
|---|---|---|---|
| | C | H | N |
| Calculated: | 78.56 | 8.35 | 6.11 |
| Found: | 78.79 | 8.32 | 6.11 |

EXAMPLE 9

Preparation of cis-dl-4,8-dimethyl- 1,2,3,4,4a,5,6,10b-octahydrobenzo[f]quinolin-3-one.

The title compound along with the trans-dl- isomer (Example 8), was prepared according to the procedures described in Example 1, Steps A, B, C, D, E, and F using p-tolylacetic acid as the starting material. Separation according to Example 1, Step G, afforded 290 mg of the title compound. Melting point 78° C.

| Elemental Analysis: | | | |
|---|---|---|---|
| | C | H | N |
| Calculated: | 78.56 | 8.35 | 6.11 |
| Found: | 78.26 | 8.56 | 5.87 |

EXAMPLE 10

Preparation of trans-dl-8-fluoro-4-methyl- 1,2,3,4,4a,5,6,10b-octahydrobenzo[f]quinolin-3-one.

The title compound along with the cis-dl- isomer (Example 11) was prepared according to the procedures described in Example 1, Steps A, B, C, D, E, and F using p-fluorophenytacetic acid as the starting material. Separation according to Example 1, Step G, afforded 244 mg of the title compound. Melting point 108°–109° C.

| Elemental Analysis: | | | |
|---|---|---|---|
| | C | H | N |
| Calculated: | 72.80 | 6.91 | 6.00 |
| Found: | 72.07 | 6.89 | 6.09 |

EXAMPLE 11

Preparation of cis-dl-8-fluoro-4-methyl- 1,2,3,4,4a,5,6,10b-octahydrobenzo[f]quinolin-3-one.

The title compound along with the trans-dl- isomer (Example 10), was prepared according to the procedures described in Example 1, Steps A, B, C, D, E, and F using p-fluorophenylacetic acid as the starting material. Separation according to Example 1, Step G, afforded 130 mg of the title compound. Melting point 136°–137° C.

| Elemental Analysis: | | | |
|---|---|---|---|
| | C | H | N |
| Calculated: | 72.08 | 6.91 | 6.00 |
| Found: | 72.30 | 7.04 | 6.06 |

EXAMPLE 12

Preparation of trans-dl-4-methyl- 1,2,3,4,4a,5,6,10b-octahydrobenzo[f]quinolin-3-one.

The title compound along with the cis-dl- isomer (Example 13), was prepared according to the procedures described in Example 1, Steps A, B, C, D, E, and F using p-phenylacetic acid as the starting material. Separation according to Example 1, Step G afforded 200 mg of the title compound. Melting point 128°–129° C.

| Elemental Analysis: | | | |
|---|---|---|---|
| | C | H | N |
| Calculated: | 78.10 | 7.96 | 6.51 |
| Found: | 77.87 | 7.85 | 6.46 |

EXAMPLE 13

Preparation of cis-dl-4-methyl-1,2,3,4,4a,5,6,10b-octahydrobenzo[f]quinolin-3-one.

The title compound along with the trans- dl-isomer (Example 12) was prepared according to the procedures described in Example 1, Steps A, B, C, D, E, and F using p-phenylacetic acid as the starting material. Separation according to Example 1, Step G, afforded the title compound. Melting point 129°–130° C.

| Elemental Analysis: | | | |
|---|---|---|---|
| | C | H | N |
| Calculated: | 78.10 | 7.96 | 6.51 |
| Found: | 78.32 | 7.04 | 6.58 |

EXAMPLE 14

Preparation of cis-dl-1,2,3,4,4a,5,6,10b-octahydrobenzo[f]quinolin-3-one.

The compound 1,2,3,4,5,6-hexahydrobenzo[f] quinolin-3-one was prepared according to the procedures described in Example 1, Steps A, B, C, and D using phenylacetic acid as the starting material.

To 94 ml of acetic acid was added 1,2,3,4,5,6-hexahydrobenzo[f]quinolin-3-one (3 g; 15 mmol) and 3 g of 5% palladium on activated carbon. The mixture was allowed to stand at room temperature for three days at an initial hydrogen pressure of 60 psi. The catalyst was removed by filtration. The filtrate was diluted with ethyl acetate and made basic with saturated $NaHCO_3$. The resulting layers were separated and the organic layer dried over $MgSO_4$ and concentrated, to afford 1.4 g (46% yield) of the title compound. Melting point 178°–179° C.

| Elemental Analysis: | | | |
|---|---|---|---|
| | C | H | N |
| Calculated: | 77.58 | 7.51 | 6.96 |
| Found: | 77.88 | 7.52 | 7.05 |

EXAMPLE 15

Preparation of trans-dl-8-fluoro- 1,2,3,4,4a,5,6,10b-octahydrobenzo[f]quinolin-3-one. The title compound was prepared according to the procedures described in Example 1, Steps A, B, C, D, F, and G using p-fluorophenylacetic acid as the starting material to afford 14.2 mg of the title compound. Melting point 262°–263° C.

| Elemental Analysis: | | | |
|---|---|---|---|
| | C | H | N |
| Calculated: | 71.21 | 6.44 | 6.39 |
| Found: | 71.17 | 6.48 | 6.29 |

EXAMPLE 16

Preparation of trans-dl-8-ethoxycarbonylethenediyl-4-methyl-1,2,3,4,4a,5,6,10b-octahydrobenzo[f]quinolin-3-one.

The compound trans-dl-8-bromo-4-methyl- 1,2,3,4,4a,5,6,10b-octahydrobenzo[f]quinolin-3-one was prepared according to the procedures described in Example 1, Steps A, B, C, D, E, F, and G. This compound (1.52 g; 5.17 mmol) and palladium (II) acetate (12 mg; 0.052 mmol), tri-(otolyl)phosphine (64 mg; 0.28 mmol), ethyl acrylate (647 mg; 6.46 mmol) and triethylamine (2.8 ml) were combined in a thick-walled tube equipped with a magnetic, non-stick Teflon® coated, stir bar. The reaction mixture was heated to 100° C. in the sealed tube and maintained there overnight. After cooling, 1N HCl was added and the green solid stirred gently with a spatula. The solids were collected by filtration and dissolved in ethanol with heating. The solution was filtered through diatomaceous earth (Celite®) and washed several times with ethanol. The volatiles were evaporated under vacuum to afford a solid yellow residue. Recrystallization of the residue from a mixture of ethyl acetate/hexanes afforded 1.24 g of the title compound as a fluffy yellow material (88% yield). Melting point 115.5°–116.5° C. High resolution Mass Spec.: 313.1659 $C_{19}H_{23}NO_3$.

EXAMPLE 17

Preparation of trans-dl-8-chloro- 1,2,3,4,4a,5,6,10b-octahydrobenzo[f]quinolin-3-one.

The title compound was prepared according to the procedures described in Example 1, Steps A, B, C, D, F, and G using p-chlorophenylacetic acid as the starting material. Melting point 231°–232° C.

| | Elemental Analysis: | | |
|---|---|---|---|
| | C | H | N |
| Calculated: | 66.24 | 5.97 | 5.94 |
| Found: | 66.44 | 6.17 | 6.06 |

EXAMPLE 18

Preparation of trans-dl-8-methoxy- 1,2,3,4,4a,5,6,10b-octahydrobenzo[f]quinolin-3-one.

The title compound was prepared according to the procedures described in Example 1, Steps A, B, C, D, and F, followed by recrystallization from ethyl acetate using p-methoxyphenylacetic acid as the starting method to afford 198 mg (38%) of an off-white highly crystalline material. Melting point 216°–217° C.

EXAMPLE 19

Preparation of trans-dl-8-methoxy-4-methyl- 1,2,3,4,4a,5,6,10b-octahydrobenzo[f]quinolin-3-one.

The title compound was prepared according to the procedures described in Example 1, Steps A, B, C, D, F, recrystallization from ethyl acetate and then E using p-methoxyphenylacetic acid as the starting material to afford 38 mg of a yellow powder. Melting point 102°–103° C.

| | Elemental Analysis: | | |
|---|---|---|---|
| | C | H | N |
| Calculated: | 72.20 | 7.40 | 6.05 |
| Found: | 72.61 | 7.59 | 5.94 |

EXAMPLE 20

Preparation of trans-dl-8-methyl- 1,2,3,4,4a,5,6,10b-octahydrobenzo[f]quinolin-3-one.

The title compound was prepared according to the procedures described in Example 1, Steps A, B, C, D, F, and G using p-tolylacetic acid as the starting material. Melting point 226°–227° C.

| | Elemental Analysis: | | |
|---|---|---|---|
| | C | H | N |
| Calculated: | 78.10 | 7.96 | 6.51 |
| Found: | 78.39 | 8.19 | 6.27 |

EXAMPLE 21

Preparation of trans-dl-1,2,3,4,4a,5,6,10b-octahydrobenzo[f]quinolin-3-one.

The title compound was prepared according to the procedures described in Example 1, Steps A, B, C, D, and F using phenylacetic acid as the starting material to afford 327 mg (30% yield) after four recrystallizations from ethyl acetate. Melting point 227°–228° C.

| | Elemental Analysis: | | |
|---|---|---|---|
| | C | H | N |
| Calculated: | 77.58 | 7.58 | 6.96 |
| Found: | 77.29 | 7.74 | 6.99 |

EXAMPLE 22

Preparation of trans-dl-8-ethoxycarbonylethanediyl-4-methyl-1,2,3,4,4a,5,6,10b-octahydrobenzo[f]quinolin-3-one.

The compound trans-dl-8-ethoxycarbonylethenediyl-4-methyl-1,2,3,4,4a,5,6,10b-octahydrobenzo[f]-quinolin-3-one was prepared according to the procedures described in Example 16. This compound (424 mg; 1.35 mmol) was combined with 50 mg of 5% palladium on activated carbon in 50 ml of ethanol in a sealed reactor at room temperature under an initial pressure of 60 p.s.i. After four hours, the catalyst is removed by filtration. The filtrate was concentrated under vacuum. The residue was subjected to flash chromatography on $SiO_2$ and elution with (5% methanol/$CH_2Cl_2$ afforded 308 mg (72%) of the title compound as a light yellow oil which crystallized on standing. Melting point 86°–88° C. High resolution Mass Spec.: 315.1840 $C_{19}H_{25}NO_3$.

EXAMPLE 23

Preparation of trans-dl-8-methoxycarbonylethenediyl-4-methyl-1,2,3,4,4a,5,6,10b-octahydrobenzo[f]quinolin-3-one.

The title compound was prepared according to the procedures described in Example 16, except that methyl acrylate was used rather than ethyl acrylate, to afford 1.18 g (94% yield). Melting point 172°–174° C.

| | Elemental Analysis: | | |
|---|---|---|---|
| | C | H | N |
| Calculated: | 72.22 | 7.07 | 4.68 |
| Found: | 71.97 | 7.87 | 4.72 |

EXAMPLE 24

Preparation of trans-dl-8-carboxyethenediyl-4 -methyl-1,2,3,4,4a,5,6,10b-octahydrobenzo[f]quinolin-3-one.

The compound trans-dl-8-ethoxycarbonylethenediyl-4 -methyl-1,2,3,4,5,6,10b-octahydrobenzo[f]quinolin-3-one was prepared according to the procedures described in Example 16. To a solution of KOH (436 mg; 7.77 mmol) in a 3:1 (V:V) mixture of methanol and water was added the ethyl ester (1.22g; 3.89 mmol). The reaction mixture was heated at reflux with stirring for one hour. The methanol was removed under vacuum and the remaining mixture acidified with 5N HCl. A resulting white precipitate was collected by filtration and washed with water. Recrystallization from ethanol afforded 741 mg (67% yield) of the title compound as a white crystalline material. Melting point 311° C. decomp.

| | Elemental Analysis: | | |
|---|---|---|---|
| | C | H | N |
| Calculated: | 71.56 | 6.71 | 4.91 |
| Found: | 71.82 | 6.57 | 4.88 |

EXAMPLE 25

Preparation of trans-dl-8-t-butylaminocarbonylethenediyl- 4-methyl-1,2,3,4,4a,5,6,10b-octahydrobenzo[f]quinolin-3-one.

A. Trans -dl-8-(2-thiopyridylcarbonylethenediyl)- 4-methyl-1,2,3,4,4a,5,6,10b-octahydrobenzo[f]quinolin-3-one.

The compound trans-dl-8-carboxyethenediyl-4 -methyl-1,2,3,4,4a,5,6,10b-octahydrobenzo[f]quinolin-3-one was prepared according to the procedures described in Example 24. A suspension of this acid (1.99 g, 6.97 mmol), triphenylphosphine (3.66 g, 1 3.95 mmol) and 2,2'-dithiodipyridine (3.07 g, 13. 95 mmols) in 30 ml of anhydrous toluene was stirred at room temperature overnight. The reaction mixture was filtered and the precipitate washed with 100 ml of diethyl ether and dried to afford 2.2 g of the subtitled compound as a pale yellow solid (81%).

B. Trans-dl-8-t-butylaminocarbonylethenediyl-4 -methyl-1,2,3,4,4a,5,6,10b-octahydrobenzo[f]quinolin-3-one.

To a stirred suspension of the thiopyridyl-ester afforded in step A, above, (440 mg; 1.13 mmol) in dry THF (11.0 ml) was added tert-butylamine (.95 ml; 9.04 mmol). The reaction mixture was stirred at room temperature for 24 hours. The mixture was filtered and the solids washed with hexanes to afford 256 mg (66.5% yield) of the title compound. Melting point 243°–245° C. decomp.

| | Elemental Analysis: | | |
|---|---|---|---|
| | C | H | N |
| Calculated: | 74.08 | 8.29 | 8.23 |
| | Elemental Analysis: | | |
|---|---|---|---|
| | C | H | N |
| Found: | 74.21 | 8.39 | 8.11 |

EXAMPLE 26

Preparation of trans-dl-8-chloro-2-(α and β)-methyl-4-methyl-1,2,3,4,4a,5,6,10b-octahydrobenzo[f]quinolin-3-one.

The compound trans-dl-8-chloro-4-methyl- 1,2,3,4,4a,5,6,10b- octahydrobenzo[f]quinolin-3-one was prepared according to the procedures described in Example 6.

To a cold (−78° C.; dry ice/isopropanol bath) stirred solution of trans-dl-8-chloro-4-methyl-1,2,3,4,4a,5,6,10b-octahydrobenzo[ f]quinolin-3-one (759 mg; 2.88 mmol) in 45 ml of dry THF was added 17.6 ml of 0.5M potassium hexmethyldisilazide (1.1 equiv.; 8.81 mmol) in toluene dropwise. After the addition was complete, the reaction mixture was stirred in the cold for an additional 45 minutes. An excess (5.0 equiv.) of methyl iodide (2.5 ml) was added to the reaction mixture. The cooling bath was removed and the reaction mixture allowed to warm to room temperature over 2 hours. The reaction was quenched by the cautious addition of water and the mixture transferred to a separatory funnel. To the mixture was added ethyl acetate and 1N HCl and the layers separated. The organic layer was washed with 1N HCl, once with saturated NaHCO$_3$ and then brine. The organic material was dried over MgSO$_4$ and evaporated under vacuum to afford 2.11 g of the title compound as a yellow solid.

The α and β isomers were separated by HPLC on silica gel using 0–75% ethyl acetate/toluene (v:v) gradient to afford 414 mg of the α-isomer (Example 26A; melting point 166°–167° C.) as a white solid and 199 mg of the β isomer (Example 26B; melting point 82°–83° C.) as a colorless solid.

| | Elemental Analysis: | | |
|---|---|---|---|
| | C | H | N |
| α-isomer | | | |
| Calculated: | 68.30 | 6.88 | 5.31 |
| Found: | 68.09 | 6.93 | 5.20 |
| β-isomer | | | |
| Calculated: | 68.30 | 6.88 | 5.31 |
| Found: | 68.05 | 6.68 | 5.55 |

EXAMPLE 27

Preparation of trans-dl-8-bromo-6,6-dimethyl- 1,2,3,4,4a,5,6,10b-octahydrobenzo[f]quinolin-3-one.

4,4-dimethyl-6-bromo-2-tetralone was prepared according to the procedures described in Example 1, Steps A and B with the exceptions that isobutylene was used in Step B rather than ethylene and that the 1:1 mixture of 4,4-dimethyl and 3,3-dimethyl regioisomeric tetralones obtained was separated by HPLC on silica gel using 0–7.5% ethyl acetate/hexanes (v:v) gradient to give the desired 4,4 -dimethyl-6-bromo-2-tetralone. The title compound was prepared from this tetralone according to the procedures described in Example 1, Steps C, D, and F and then recrystallization from ethyl acetate to yield 109.3 mg of a white solid. Melting point 281°–282° C.

| Elemental Analysis: | | | |
|---|---|---|---|
| | C | H | N |
| Calculated: | 58.45 | 5.89 | 4.54 |
| Found: | 58.68 | 5.77 | 4.44 |

EXAMPLE 28

Preparation of trans-dl-8-bromo-4,6,6-trimethyl- 1,2,3,4,4a,5,6,10b-ocathydrobenzo[f]quinolin-3-one.

A mixture of trans and cis-dl-8-bromo-6,6-dimethyl- 1,2,3,4,4a,5,6,10b-octahydrobenzo[f]quinolin-3-one was obtained by concentration of the filtrates of the ethyl acetate recrystallizations of trans-dl-8-bromo-6,6-dimethyl- 1,2,3,4,4a,5,6,1 0b-octahydrobenzo[f]quinolin-3-one (Example 27). The title compound was prepared from this material along with the cis-dl-isomer (Example 29) using the procedures described in Example 1, Steps E and G to afford 67.2 mg of a white solid. Melting point 133°–136° C.

| Elemental Analysis: | | | |
|---|---|---|---|
| | C | H | N |
| Calculated: | 59.64 | 6.26 | 4.35 |
| Found: | 59.50 | 6.21 | 4.55 |

EXAMPLE 29

Preparation of cis-dl-8-bromo-4,6,6-trimethyl- 1,2,3,4,4a,5,6,10b-octahydrobenzo[f]quinolin-3-one.

A mixture of trans and cis-dl-8-bromo-6,6-dimethyl- 1,2,3,4,4a,5,6,10b-octahydrobenzo[f]quinolin-3-one was obtained by concentration of the filtrates of the ethyl acetate recrystallizations of trans -dl-8-bromo-6,6-dimethyl- 1,2,3,4,4a,5,6,10b-octahydrobenzo[f]quinolin-3-one (Example 27). The title compound was prepared from this material along with the trans-dl-isomer (Example 28) using the procedures described in Example 1, Steps E and G to afford 67.2 mg of a white solid. Melting point 177°–180° C.

| Elemental Analysis: | | | |
|---|---|---|---|
| | C | H | N |
| Calculated: | 59.64 | 6.26 | 4.35 |
| Found: | 59.85 | 6.16 | 4.28 |

EXAMPLE 30

Preparation of trans-dl-8-t-butyl- 1,2,3,4,4a,5,6,10b-octahydrobenzo[f]quinolin-3-one.

A. 6-tert-butyl-2-naphthol.

A 2 L round bottomed flask was charged with freshly fused zinc chloride (45.0 g), β-naphthol (150.0 g; 1.04 mol) and hexanes (450 ml). The mixture was stirred vigorously while adding t-butyl chloride (150.0 g; 1.62 mol) dropwise over 30 min. When the reaction mixture was gradually heated to reflux, a solution was not obtained. The reaction mixture was cooled to room temperature and 100 ml of $CH_2Cl_2$ was added. The reaction mixture was refluxed overnight, cooled and concentrated under vacuum to afford a white solid. The solid was refluxed with 1800 ml of 10% NaOH, filtered, and allowed to cool. The white sodium salt which precipitated was collected by filtration. The solid collected by filtration was stirred with excess 5.0M HCl and the resulting phenol was collected by filtration and washed with 2 L of water. Recrystallization from heptane afforded 30.67 g of the subtitle compound as a white solid.

B. 6-t-butyl-2-methoxynaphthalene.

To a 2 L round bottomed flask was added 6-t-butyl-2-naphthol (30.67 g; 0.153 mmol) and 550 ml of 15% KOH in water. The solution was stirred while adding dimethyl sulfate (6.0 equiv.) dropwise over 30 min. After the addition was complete, the mixture was allowed to stir for 2 hrs. The solids were collected on a filter and washed with water to afford 28.97 g (88% yield) of the subtitle compound.

C. 6-t-butyl-2-tetralone.

To a stirred solution of 6-t-butyl-2-methoxynaphthalene (28.97 g; 0.135 mmol) in 350 ml of anhydrous ethanol was added sodium spheres (36 g; 11.5 equiv.) over 2 hrs. at a rate so as to maintain a gentle reflux. The viscous reaction mixture was stirred until all of the sodium had dissolved. The mixture was cooled and 140 ml of water was cautiously added. Concentrated HCl (275 ml) was added and the reaction mixture was refluxed for 30 minutes. After cooling, the reaction mixture was filtered and the aqueous layer was extracted 3 times with toluene. Evaporation of the volatiles under vacuum afforded 28.1 g of a red viscous oil. The oil was taken up in 300 ml of diethyl ether and stirred with 50 ml of saturated aqueous $NaHSO_3$ overnight. The resulting white precipitate was collected by filtration and washed several times with hexanes. This material was partially dissolved in 500 ml of $H_2O$ and 200 ml of diethyl ether was added. The mixture was vigorously stirred and 300 ml of saturated aqueous $Na_2CO_3$ added. The mixture was stirred for one hour, the layers were separated, and the aqueous layer was extracted 3 times with diethyl ether. The combined organic layers were combined, washed with brine, dried over $MgSO_4$ and concentrated under vacuum to afford 5.74 g of the subtitle compound as an orange oil which crystallized slowly on standing.

D. 6-t-butyl-2-pyrrolidinyl-3,4-dihydronaphthalene.

To a stirred solution of 6-t-butyl-2-tetralone (5.74 g; 28.37 mmol) in 100 ml of toluene was added 1.5 equiv. of pyrrolidine (3.56 ml; 42.56 mmol). A 100 mg portion of p-toluenesulfonic acid was added and the mixture was refluxed. The water eliminated during the reaction was collected by a Dean Stark trap. After a reflux time of 3.5 hours, concentration of the volatiles under vacuum afforded 7.31 g of the subtitle compound as a purple solid.

E. 8-t-butyl-1,2,3,4,5,6-hexahydrobenzo[f] quinolin-3-one.

To 6-t-butyl-2-pyrrolidinyl-3,4-dihydronaphthalene (7.25 g; 28.37 mmol) was added 3.0 equiv. of acrylamide (6.05 g; 85.11 mmol). The reaction mixture was stirred at 89° C. overnight. The temperature was then increased to 130° C. and held there for 20 minutes. Water (100 ml) was cautiously added and the reaction mixture was cooled to room temperature. The resulting solid was triturated with water and collected on a filter to afford a brown solid. The solid was recrystallized twice from dimethyl formamide (DMF)/$H_2O$ to afford the subtitle compound. Melting point 265°–268° C. decomp.

F. Trans-all-8-t-butyl-1,2,3,4,4a,5,6,10b-octahydrobenzo[f]quinolin-3-one.

To a cold (0° C.) stirred solution of 8-t-butyl- 1,2,3,4,5,6,-hexahydrobenzo[f]quinolin-3-one (4.00 g; 15.66 mmol) and triethylsilane (7.29 g; 62.66 mmol) in 90 ml of $CH_2Cl_2$ was added 45 ml of trifluoroacetic acid. The cooling bath was removed and the mixture stirred at room temperature for 24 hours. The reaction mixture was poured cautiously into saturated $NaHCO_3$, shaken, and the layers separated. The organic layer was washed once with $NaHCO_3$, dried over $Na_2SO_4$ and concentrated under vacuum to afford 5.86 g of a brown solid. Recrystallization from ethyl acetate afforded the subtitle compound (2.5g; 62% yield) as a beige crystalline material. Melting point greater than 280° C.

| | Elemental Analysis: | | |
|---|---|---|---|
| | C | H | N |
| Calculated: | 79.33 | 9.01 | 5.44 |
| Found: | 79.36 | 9.16 | 5.49 |

EXAMPLE 31

Preparation of trans-dl-8-t-butyl-4-methyl- 1,2,3,4,5,6,10b-octahydrobenzo[f]quinolin-3-one.

The title compound was prepared according to the procedures described in Example 30, Steps A, B, C, D, E and F and then N-methylated according to the procedures described in Example 1, Step E using 1,2-dimethoxyethane as the solvent, to afford 1.14 g (73% yield) of a tan solid. Melting point 183°–184° C.

| | Elemental Analysis: | | |
|---|---|---|---|
| | C | H | N |
| Calculated: | 79.66 | 9.29 | 5.16 |
| Found: | 80.08 | 9.31 | 4.99 |

EXAMPLE 32

Preparation of trans-dl-8-fluoro-4,10b-dimethyl- 1,2,3,4,4a,5,6,10b-octahydrobenzo[f]quinolin-3-one.

A. 6-fluoro-2-pyrrolidinyl-3,4-dihydronaphthalene.

The subtitle compound was prepared according to the procedures described in Example 1, Steps A, B and C using p-fluorophenylacetic acid as the starting material.

B. 6-fluoro-1-methyl-2-pyrrolidinyl-3,4-dihydronaphthalene.

To 6-fluoro-2-pyrrolidinyl-3,4-dihydronaphthalene (13 g; 60.8 mmol) in 200 ml of dry tetrahydrofuran (THF) was added methyliodide (30 ml; 482 mmol) and the mixture refluxed for 2 hours. The reaction mixture was allowed to cool with stirring while crystallization took place. The solids were collected by filtration to afford the subtitle compound.

C. 6-fluoro-1-methyl-2-tetralone.

To the 6-fluoro-1-methyl-2-pyrrolidinyl-3,4-dihydronaphthalene afforded above in Step B in 1700 ml of ethyl acetate was added sodium acetate (10.2 g; 124.4 mmol), acetic acid (10.2 ml; 178.2 mmol) and 102 ml of water. The reaction mixture was stirred at room temperature for 4 hours. The layers were separated and the organic layer was washed with brine, 5% $NaHCO_3$, and brine. The organic layer was dried over $MgSO_4$ and was concentrated to afford 7.9 g of the subtitle compound as a dark orange-red oil (60% yield).

D. 8-fluoro-10b-methyl-1,2,3,4,6,10b-hexahydrobenzo[f]quinolin-3-one.

To 6-fluoro-1-methyl-2-tetralone (7.06 g; 39.6 mmol) in a round bottomed flask was added p-toluenesulfonic acid (1.23 g; 6.5 mmol) and the mixture was stirred at room temperature under nitrogen for 15 minutes. Acrylamide (5.62 g; 79.2 mmol) was added and the reaction mixture was heated to 88°–90° C. under nitrogen for three days. The mixture was diluted with ethyl acetate and water and stirred at room temperature for 1 hour. The resulting layers were separated. The organic layer was washed three times with water, dried over $MgSO_4$ and concentrated to a viscous oil. The crude product was crystallized from ethyl acetate to afford 1.59 g (17% yield) of the subtitle compound. Melting point 202° C.

| | Elemental Analysis: | | |
|---|---|---|---|
| | C | H | N |
| Calculated: | 72.71 | 6.10 | 6.06 |
| Found: | 72.45 | 6.14 | 6.03 |

E. 8-fluoro-4,10b-dimethyl-1,2,3,4,6,10b-hexahydrobenzo[f]quinolin-3-one.

8-fluoro-10b-methyl-1,2,3,4,6,10b-hexahydrobenzo[f]quinolin-3-one (1.38 g; 6mmol) was added to a suspension of NaH (475 mg; 20 mmol) in glyme (15 ml). The mixture was refluxed for 1.5 hours and cooled quickly to room temperature. Methyl iodide (15 ml) was added and the mixture refluxed for 4 hours, then allowed to cool to room temperature. After addition of water, the mixture was concentrated to near dryness. The residue was partitioned between ethyl acetate and water. The organic layer was washed three times with water, dried over $MgSO_4$ and concentrated under vacuum. Recrystallization from hexane afforded 737 mg (56% yield) of the subtitle compound. Melting point 110°–111° C.

| | Elemental Analysis: | | |
|---|---|---|---|
| | C | H | N |
| Calculated: | 73.45 | 6.57 | 5.71 |
| Found: | 73.72 | 6.84 | 5.86 |

F. 8-fluoro-4,10b-dimethyl-1,2,3,4,4a,5,6,10b-octahydrobenzo[f]quinolin-3-one.

Triethylsilane (1 ml; 6.12 mmol) was added to 8-fluoro-4,10b-dimethyl-1,2,3,4,6,10b-hexahydrobenzo[f]quinolin-3-one (500 mg; 2.04 mmol) in $CH_2Cl_2$ (15 ml) at room temperature. The reaction mixture was cooled to 0° C. and trifluoroacetic acid (2.6 ml) was added. After stirring at room temperature for four days, the reaction mixture was diluted with $CH_2Cl_2$ and treated with saturated $NaHCO_3$. The resulting layers were separated and the organic layer was washed with saturated $NaHCO_3$, dried over $MgSO_4$ and concentrated under vacuum to a yellow oil.

G. Trans-dl-8-fluoro-4,10b-dimethyl-1,2,3,4,4a,5,6,10b-octahydrobenzo[f]quinolin-3-one.

The mixture obtained above in Step F was separated by column chromatography on $SiO_2$ (elution with ethyl acetate/hexanes 9:1 (v:v)). The appropriate fractions containing the desired product were evaporated to near dryness and diluted with hexanes. The resulting crystals were collected by filtration to afford 190 mg of the subtitle compound. Melting point 130°–131° C.

| Elemental Analysis: | | | |
|---|---|---|---|
| | C | H | N |
| Calculated: | 72.85 | 7.34 | 5.66 |
| Found: | 72.71 | 7.48 | 5.73 |

EXAMPLE 33

Preparation of cis-dl-8-fluoro-4,10b-dimethyl- 1,2,3,4,4a,5,6,10b-octahydrobenzo[f]quinolin-3-one.

The title compound was prepared along with the trans-dl-isomer according to the procedures described in Example 32, Steps A–F.

The mixture obtained in Example 32, Step F was separated by column chromatography on SiO$_2$ (elution with ethyl acetate/hexanes 9:1 (v:v)). The appropriate fractions containing the desired product were evaporated to near dryness and diluted with hexanes. The resulting crystals were collected by filtration to afford the title compound.

EXAMPLE 34

Preparation of trans-dl-8-chloro-4,10b-di-methyl- 1,2,3,4,4a,5,6,10b-octahydrobenzo[f]-quinolin-3-one.

The title compound was prepared along with the cis-dl-isomer (Example 35) according to the procedures described in Example 32, Steps A, B, C, D, E and F using p-chlorophenylacetic acid as the starting material. Column chromatography according to Example 32, Step G afforded 523 mg of the title compound. Melting point 94° C.

| Elemental Analysis: | | | |
|---|---|---|---|
| | C | H | N |
| Calculated: | 68.30 | 6.88 | 5.31 |
| Found: | 68.51 | 6.67 | 5.36 |

EXAMPLE 35

Preparation of cis-dl-8-chloro-4,10b-dimethyl- 2,3,4,4a,5,6,10b-octahydrobenzo[f]quinolin-3-one.

The title compound was prepared along with the trans-dl-isomer (Example 34) according to the procedures described in Example 32, Steps A, B, C, D, E, and F using p-chlorophenylacetic acid as the starting material. Column chromatography according to Example 32, Step G afforded 145 mg of the title compound.

| Elemental Analysis: | | | |
|---|---|---|---|
| | C | H | N |
| Calculated: | 68.30 | 6.88 | 5.31 |
| Found: | 68.09 | 6.76 | 5.11 |

EXAMPLE 36

Preparation of trans-dl-10b-methyl- 1,2,3,4,4a,5,6,10b-octahydrobenzo[f]quinolin-3-one.

A. 10b-methyl-1,2,3,4,6,10b-hexahydrobenzo[f] quinolin-3-one.

By following the procedures described in Example 32, Steps A, B, C and D, except using phenylacetic acid as the starting material, and using column chromatography on SiO$_2$, rather than recrystallization from ethyl acetate, the subtitle compound was prepared as a white crystalline solid. Melting point 123°–124° C.

| Elemental Analysis: | | | |
|---|---|---|---|
| | C | H | N |
| Calculated: | 78.84 | 7.09 | 6.57 |
| Found: | 78.82 | 6.95 | 6.58 |

B. Trans-dl-10b-methyl-1,2,3,4,6,10b-octahydrobenzo[f]quinolin-3-one.

To 10b-methyl-1,2,3,4,6,10b-hexahydrobenzo[f]quinolin-3-one (500 mg; 2.3 mmol) in 50 ml of acetic acid was added 500 mg of 5% palladium on carbon. The reaction mixture was stirred overnight at room temperature under an initial hydrogen pressure of 60 p.s.i. The reaction mixture was filtered and concentrated to dryness. The residue was partitioned between ethyl acetate and water. The organic layer was washed twice with saturated NaHCO$_3$, and with water, and then dried over MgSO$_4$ and concentrated under vacuum. The residue was triturated with ether to afford 180 mg (36% yield) of the subtitle compound. Melting point 178°–179° C.

| Elemental Analysis: | | | |
|---|---|---|---|
| | C | H | N |
| Calculated: | 78.10 | 7.96 | 6.51 |
| Found: | 78.38 | 8.02 | 6.36 |

EXAMPLE 37

Preparation of trans-dl-4,10b-dimethyl- 1,2,3,4,4a,5,6,10b-octahydrobenzo[f]quinolin-3-one.

By following the procedures described in Example 36, trans-dl-10b-methyl-1,2,3,4,4a,5,6,10b-octahydrobenzo[f]quinolin-3-one was prepared. To 4 ml of glyme was added NaH (31 mg; 1.26 mmol) and trans-dl-10b-methyl- 1,2,3,4,4a,5,6,10b-octahydrobenzo[f]quinolin-3-one (130 mg; 0.6 mmol). The reaction mixture was refluxed for 1.5 hours. After cooling to room temperature, 10 ml of methyl iodide was added and the reaction mixture refluxed for 3 hours. Water was added and the mixture concentrated to near dryness. The residue was partitioned between ethyl acetate/water. The organic layer was washed three times with water, dried over MgSO$_4$ and concentrated under vacuum. The residue was triturated with petroleum ether to afford 60 mg (44% yield) of the title compound. Melting point 93° C.

| Elemental Analysis: | | | |
|---|---|---|---|
| | C | H | N |
| Calculated: | 78.56 | 8.35 | 6.11 |
| Found: | 78.29 | 8.16 | 6.03 |

EXAMPLE 38

Preparation of trans-dl-8-chloro-10b-methyl- 1,2,3,4,4a,5,6,10b-octahydrobenzo[f]quinolin-3-one.

By following the procedures described in Example 32, Steps A, B, C, D, and F except using p-chlorophenylacetic acid as the starting material, the compound 8-chloro-10b-methyl- 1,2,3,4,4a,5,6,10b-octahydrobenzo[f]quinolin-3-one was prepared as a mixture of cis and trans isomers.

The mixture was purified by HPLC (Reverse phase, CN), eluting with THF: isooctane (48% THF by volume) to afford 32 mg of the title compound.

| Elemental Analysis: | | | |
|---|---|---|---|
| | C | H | N |
| Calculated: | 67.33 | 6.46 | 5.61 |
| Found: | 67.53 | 6.35 | 5.73 |

EXAMPLE 39

Preparation of cis-dl-8-chloro-10b-methyl- 1,2,3,4,4a,5,6, 10b-octahydrobenzo[f]quinolin-3-one.

The title compound was prepared along with the trans-dl-isomer (Example 38) according to the procedures described in Example 38. The cis-dl-isomer was also obtained by HPLC purification using the procedures described in Example 38, followed by trituration with diethyl ether.

EXAMPLE 40

Preparation of trans- and cis- R (−) 8-chloro-10b-methyl- 1,2,3,4,4a,5,6,10b-octahydrobenzo[f]quinolin-3-one.

A. 6-chloro-1-methyl-2-tetralone.

By following the procedures described in Example 32, Steps A, B and C, except using p-chlorophenylacetic acid as the starting material, the subtitle compound was prepared.

B. 1-methyl-2-(α-methylbenzylamino)-6-chloro-1,2d-idehydrotetralin.

To 500 ml of toluene was added 6-chloro-methyl- 2-tetralone (50.0 g; 0.256 mol) and (R)-(+)-1 -phenylethylamine (35 ml; 0.27 mol). The mixture was heated to reflux for 4 hours with azeotropic removal of water. The solvent was removed under vacuum to afford 79 g of the subtitle compound, along with its imine tautomar, as a yellow oil which was used without further purification.

C. (5S)-5,6,7,8,9,10-hexahydro-8-hydroxy-2 -chloro-5,8-dimethyl-5,9-methanobenzocycloocten-11-one.

To a stirred solution of 1-methyl-2-(α-methylbenzy-lamino)-6-chloro-1,2-didehydrotetralin (79 g; 0.25 mol.) in 500 mL of THF was added methyl vinyl ketone (23 mL; 0.28 mol.). The solution was stirred at ambient temperature, under argon atmosphere, in the dark for 96 hours. Aqueous acetic acid (20%, 500 mL) was added and the mixture stirred for 2 hours. The reaction mixture was partitioned between ethyl acetate and water. The organic phase was washed with saturated $Na_2CO_3$, and dried over $Na_2SO_4$. The solvent was removed under vacuum to afford 82 g of the subtitle compound as brown oil which was used without further purification.

D. (R) (+) 8-chloro-10b-methyl-1,2,3,5,6,10b-hexahydro-phenanthren- 3-one.

To a stirred solution of sodium ethoxide prepared from sodium (6.5 g.) in ethanol (500 ml) was added the subtitle compound (82 g) from Step C. The solution was heated at 50° C. for 3 hours under nitrogen atmosphere. The solution was cooled to ambient temperature and partitioned between diethyl ether and water. The organic phase was washed with brine and was dried over $Na_2SO_4$ and concentrated under vacuum. The residue was purified by chromatography on $SiO_2$ (eluting with 25% ethyl acetate in hexanes) to afford 34 g of the subtitle compound as a brown oil which solidified upon standing.

E. (R) 3-[1-1-methyl-6-chloro-2-tetralone)] propanoic acid.

To a stirred mixture of $RuCl_3 \cdot _nH_2O$ (620 mg, 2.99 mmol.) in a solvent mixture (200 ml) of 2 parts carbon tetrachloride, 3 parts acetonitrile and 2 parts water was added periodic acid (20.45 g; 89.7 mmol). The mixture was cooled to 0° C. and stirred for 15 minutes. To the mixture was slowly added the subtitle compound from Step D (3.7 g; 14.95 mmol) in acetonitrile and the mixture stirred at 0° C. for 3 hours. 2-propanol (20 mL) was added and the mixture stirred for 1 hour. The reaction mixture was partitioned between ethyl acetate and water and the aqueous phase extracted three times with ethyl acetate. The combined organic layers were filtered through diatomaceous earth and the filter cake washed with ethyl acetate. The solution was concentrated under vacuum to afford 1.74 g of the subtitle compound which was used without further purification.

F. (R) (+)-8-chloro-10b-methyl-1,2,3,4,6,10b-hexahydrobenzo[f]quinolin-3-one.

To a stirred solution of the subtitle compound from Step E (1.74 g; 6.457 in 15 ml of 2-propanol was added ammonia (1 mL) and the tube reactor sealed. The reaction mixture was heated to 180° C. for 15 minutes. The mixture was cooled to room temperature and was concentrated under vacuum to a brown glassy solid. The solid was taken up in ethyl acetate, filtered through $SiO_2$, eluting with ethyl acetate, to afford the subtitle compound as a pale solid. A sample was crystallized from diethyl ether/hexane to afford 219 mg of the subtitle compound. Melting point 61°–63° C.

| Elemental Analysis: | | | |
|---|---|---|---|
| | C | H | N |
| Calculated: | 67.88 | 5.70 | 5.65 |
| Found: | 67.54 | 5.65 | 5.44 |

Optical rotation: 589 nm=−40.32°

(C=1, methanol) 365 nm=−185.48°

G. 8-chloro-10b-methyl-1,2,3,4,4a,5,6,10-octahydrobenzo[f]quinolin-3-one.

To a stirred solution of the subtitle compound from Step F (776 mg; 3.1 mmol) and triethylsilane (4.95 ml; 31 mmol) in $CH_2Cl_2$ at 0° C. was added trifluoroacetic acid (4.82 ml; 6.26 mmol). The solution was slowly warmed to room temperature and stirred for 48 hours. The reaction mixture was diluted with ethyl acetate, neutralized with $Na_2CO_3$, extracted with ethyl acetate and concentrated under vacuum to afford 790 mg of crude product that included the subtitle compound.

H. Trans-8-chloro-10b-methyl-1,2,3,4,4a,5,6,10-octhydrobenzo[ f]-quinolin-3-one.

Chromatography on $SiO_2$ (ethyl acetate as eluent) of the crude product from Step G afforded 341 mg of the subtitle compound. Melting point 135°–137° C.

| Elemental Analysis: | | | |
| --- | --- | --- | --- |
| | C | H | N |
| Calculated: | 67.33 | 6.46 | 5.61 |
| Found: | 67.41 | 6.55 | 5.36 |

Optical rotation: 589 nm=+113.86°
(C=1, CHCl$_3$) 365 nm=+371.29°

EXAMPLE 41

Preparation of cis-8-chloro-10b-methyl- 1,2,3,4,4a,5,6,10-octahydrobenzo[f]quinolin-3-one.

The title compound was prepared along with the trans-isomer (Example 40) by the procedures described in Example 40, Steps A–G. Chromatography on SiO$_2$ (ethyl acetate as eluent) of the crude product from Example 40, Step G afforded 91 mg of the title compound. Melting point 178°–181° C.

| Elemental Analysis: | | | |
| --- | --- | --- | --- |
| | C | H | N |
| Calculated: | 67.33 | 6.46 | 5.61 |
| Found: | 66.73 | 6.73 | 5.36 |

Optical rotation: 589 nm=+199.10°
(C=1, CHCl$_3$) 365 nm=+660.63°

EXAMPLE 42

Preparation of trans-4-ethyl-10b-methyl- 1,2,3,4,4a,5,6,10b-octahydrobenzo[f]quinolin-3-one.

By following the procedures described in Example 40, Steps A, B, C, D, E and F using phenylacetic acid as the starting material and using ethylamine rather than ammonia, and digylme rather ethylene glycol in Step F, the compound 4-ethyl-10b-methyl-1,2,3,4,6,10b-hexahydrobenzo[f]quinolin-3one was prepared. This hexahydrobenzo[f]quinolin-3-one was hydrogenated by following the procedures described Example 22 except that the reaction was carried out at 70° C. over 7 hours to afford a crude reaction mixture. The reaction mixture was filtered and the solvents evaporated under vacuum to afford a glassy solid residue. The crude product was purified by chromatography on SiO$_2$ (gradient elution from 100% hexanes to 100% CHCl$_3$) to afford 92 mg of the title compound as a colorless oil.

| Elemental Analysis: | | | |
| --- | --- | --- | --- |
| | C | H | N |
| Calculated: | 78.97 | 8.70 | 5.76 |
| Found: | 79.07 | 8.90 | 5.56 |

EXAMPLE 43

Preparation of trans-4-n-butyl-10b-methyl- 1,2,3,4,4a,5,6,10b-octahydrobenzo[f]quinolin-3-one.

By following the procedures described in Example 40, Steps A, B, C, D, E and F using phenylacetic acid as the starting material and in Step F using n-butylamine rather than ammonia and dimethoxyethane rather than ethylene glycol, the compound 4-n-butyl-10b-methyl-1,2,3,4,6,10b-hexahydrobenzo[f]quinolin-3-one was prepared. This hexahydrobenzo[f]quinolin-3-one was hydrogenated by following the procedures described Example 22 except that the reaction was carried out at 60° C. over 7 hours and worked up according to the procedures described in Example 42 to afford 61 mg of the title compound as a colorless oil.

| Elemental Analysis: | | | |
| --- | --- | --- | --- |
| | C | H | N |
| Calculated: | 77.10 | 9.35 | 5.00 |
| Found: | 77.44 | 9.28 | 4.95 |

EXAMPLE 44

Preparation of trans-4-(4-methoxybenzyl-8-chloro- 10b-methyl-1,2,3,4,4a,5,6,10b-octahydrobenzo[f]quinolin-3one.

A. (R) 3- [1-(1-methyl-6-chloro-2-tetralone)] propanoic acid.

By following the procedures described in Example 40, Step A, B, C, D and E, using p-chlorophenyl acetic acid as the starting material, the compound 3-[-(methyl-6-chloro-2-tetralone)] propanoic acid was prepared.

B. 4-(4-methoxybenzyl) -8-chloro-10b-methyl- 1,2,3,4,6,10b-hexa-hydrobenzo[f]quinolin-3-one.

To 40 ml of dimethoxyethane was added 3-[1-(1 -methyl-6-chloro-2-tetralone)]-propanoic acid (2 g) and p-methoxybenzylamine (5 ml) in a sealed tube reactor. The solution was heated at 120° C. overnight. After allowing the reaction mixture to cool to room temperature, the solvent was removed under vacuum. The residue was dissolved in CHCl$_3$, washed sequentially with 1N HCl, water, saturated NaHCO$_3$, and brine. The organic phase was dried over Na$_2$SO$_4$ and concentrated under vacuum. The residue was chromatographed on SiO$_2$ (gradient elution from 100% hexanes to 100% ethyl acetate) to afford 394 mg of the subtitle compound as an oil.

C. Trans-4-(4-methoxybenzyl)-8-chloro-10b-methyl- 1,2,3,4,4a,5,6,10b-octahydrobenzo[f]quinolin-3-one.

To a stirred solution of subtitle compound from Step B (693 mg) in CH$_2$Cl$_2$ (2.5 mL) under a nitrogen atmosphere was added triethylsilane (1.4 ml) The reaction mixture was stirred for 15 minutes. To the solution was added 1.5 mL of trifluoroacetic acid and the reaction mixture stirred at room temperature overnight. The reaction mixture was partitioned between CHCl$_3$ and saturated NaHCO$_3$. The organic phase was dried over Na$_2$SO$_4$ and the solvent removed under vacuum. The residue was purified by chromatography on SiO$_2$ (25% ethyl acetate in hexanes as eluent). The product containing fractions were evaporated under vacuum to afford 459 mg of the subtitle compound as a foam. Melting point 55°–60° C.

| Elemental Analysis: | | | |
| --- | --- | --- | --- |
| | C | H | N |
| Calculated (+½ mol H$_2$O) | 69.74 | 6.65 | 3.70 |
| Found: | 70.27 | 6.49 | 3.68 |

EXAMPLE 45

Preparation of trans-4-methyl-10b-methyl- 1,2,3,4,4a,5,6,10b-octahydrobenzo[f]quinolin-3-one.

By following the procedures described in Example 40, Steps A, B, C, D, E and F using phenylacetic acid as the starting material and in Step F using methylamine rather than ammonia and diglyme rather than ethylene glycol, the compound 4-methyl-10b-methyl-1,2,3,4,6,10b-hexahydrobenzo[f]quinolin- 3-one was prepared. This hexahydrobenzo[f]quinolin-3-one was hydrogenated by following the procedures described in Example 22 except that the reaction was carried out at 60° C. over 7 hours. The reaction mixture was filtered and solvent evaporated under vacuum. The residue was purified by chromatography on $SiO_2$ ($CHCl_3$ as eluent) followed by recrystaliization from ethyl acetate/hexanes to afford 154 mg of the title compound. Melting point 111°–113° C.

| | Elemental Analysis: | | |
|---|---|---|---|
| | C | H | N |
| Calculated: | 78.56 | 8.35 | 6.11 |
| Found: | 78.33 | 8.62 | 6.14 |

EXAMPLE 46

Preparation of trans-dl-9-nitro-1,2,3,4,4a,5,6,10b-octahydrobenzo[ f]quinolin-3-one.

The compound trans-dl-1,2,3,4,4a,5,6,10b-octahydrobenzo[ f]quinolin-3-one was prepared according to the procedures described in Example 21. To this compound (8.0 g; 39.75 mmol) in 320 ml of a mixture of 1:1 (V:V) glacial acetic acid and concentrated sulfuric acid at 0° C. was added 1.4 equivalents of 90% fuming nitric acid at a rate which did not allow the temperature to rise above 10° C. The mixture was stirred for 30 minutes at 0° C. and then was poured onto ice. The resulting solid was collected by filtration and recrystallized from a DMF/water mixture to yield 5.40 g (55%) of the titled compound as a yellow solid. Melting point >300° C.

| | Elemental Analysis: | | |
|---|---|---|---|
| | C | H | N |
| Calculated: | 63.40 | 5.73 | 11.38 |
| Found: | 63.61 | 5.97 | 11.39 |

EXAMPLE 47

Preparation of trans-dl-9-nitro-4-methyl- 1,2,3,4,4a,5,6, 10b-octahydrobenzo[f]quinolin-3-one.

The compound trans-dl-4-methyl-1,2,3,4,4a,5,6,10b-octahydrobenzo[ f]quinolin-3-one was prepared according to the procedures described in Example 12. The title compound was prepared according to the procedure described in Example 46 using trans-dl-4-methyl-1,2,3,4,4a,5,6,10b-octahydrobenzo[ f]quinolin-3-one as the starting material except that the reaction was quenched with water and the product was recrystallized from ethyl acetate/hexanes. Melting point 172°–172.5° C.

| | Elemental Analysis: | | |
|---|---|---|---|
| | C | H | N |
| Calculated: | 64.60 | 6.20 | 10.76 |
| Found: | 64.80 | 6.34 | 10.85 |

EXAMPLE 48

Preparation of trans-dl-9-amino-4-methyl- 1,2,3,4,4a,5,6, 10b-octahydrobenzo[f]quinolin-3-one.

The compound trans-dl-9-nitro-4-methyl- 1,2,3,4,4a,5,6, 10b-octahydrobenzo[f]quinolin-3-one was prepared according to the procedures described in Example 47. This compound (700 mg, 2.69 mmol) was dissolved in 100 ml of ethanol and 100 mg of 10% palladium on carbon was added. The reaction mixture was hydrogenated for 1 hour under 42 psi of hydrogen. The mixture was filtered and the filtrate concentrated under vacuum to give a light tan solid which was recrystallized from ethyl acetate/hexanes to give 308 mg of the titled compound as a white solid. Melting point 213°– 214.5° C.

| | Elemental Analysis: | | |
|---|---|---|---|
| | C | H | N |
| Calculated: | 73.01 | 7.88 | 12.16 |
| Found: | 73.22 | 8.02 | 12.20 |

EXAMPLE 49

Preparation of trans-dl-9-chloro-4-methyl- 1,2,3,4,4a,5,6, 10b-octahydrobenzo[f]quinolin-3-one.

The compound trans-dl-9-amino-4-methyl- 1,2,3,4,4a,5, 6,10b-octahydrobenzo[f]quinolin-3-one was prepared according to the procedures described in Example 48. To a 0° C. solution of this compound (74 mg, 0.321 mmol) in 0.3 ml of concentrated HCl was added sodium nitrite (23 mg, 0.324 mmol) in 0.15 ml of water. The reaction mixture was stirred at 0° C. for 30 minutes then was added to a 0° C. solution of copper(I) chloride (35 mg, 0.353 mmol) in 0.2 ml of concentrated HCl. The reaction mixture was allowed to warm to room temperature gradually over 2.5 hours then was heated to 60° C. for 30 minutes. After cooling, the mixture was partitioned between $CHCl_3$ and saturated NaCl. The organic layer was dried over $Na_2SO_4$ and concentrated under vacuum to give 65 mg of a solid material. The title compound was obtained as a white solid (59 mg) after flash chromatography on $SiO_2$ (10% isopropanol/ethyl acetate). Melting point 228°– 230° C.

| | Elemental Analysis: | | |
|---|---|---|---|
| | C | H | N |
| Calculated: | 67.33 | 6.46 | 5.61 |
| Found: | 67.19 | 6.57 | 5.53 |

EXAMPLE 50

Preparation of trans-dl-8-chloro-3,4,4a,5,6,10b-hexahydrobenzo[ f]quinolin-3-one and trans-dl-8-chloro- 2,3,4,4a, 5,6-hexahydrobenzo[f]quinolin-3-one.

A. Trans-dl-4-t-butyloxycarbonyl-8-chloro- 1,2,3,4,4a,5,6,10b-octahydrobenzo[f]quinolin-3-one.

The compound trans-dl-8-chloro- 1,2,3,4,4a,5,6,10b-octahydrobenzo[f]quinolin-3-one was prepared according to the procedures described in Example 17. To this compound (1.56 g, 6.62 mmol) in 40 ml of anhydrous 1,2-dimethoxyethane (1,2-DME) was added 380 mg of sodium hydride as a 60% dispersion in mineral oil. The mixture was refluxed for 1 hour under a nitrogen atmosphere then cooled to room temperature. A solution of di-t-butyl dicarbonate (1.74 g, 7.94 mmol) in 10 ml of anhydrous 1,2-DME was added and the mixture refluxed for 1 hour. The mixture was cooled and water was added cautiously followed by diethyl ether. The layers were separated and the aqueous layer extracted with diethyl ether. The combined organic layers were washed with saturated NaCl, dried over $Na_2SO_4$, and concentrated to give an orange semi-solid which was purified by column chromatography ($SiO_2$, 1:1 ethyl acetate/hexanes) to afford 1.2 g (54%) of the subtitled compound as a white solid.

B. Trans-dl-4-t-butyloxycarbonyl-2-phenylseleno-8-chloro-1,2,3,4,4a,5,6,10b-octahydrobenzo[f]quinolin-3-one.

To the protected lactam afforded in Step A (1.2 g, 3.58 mmol) in 20 ml of anhydrous THF at −78° C. was added dropwise a 0.5M solution of potassium hexamethyldisilazide (14.3 ml, 7.16 mmol) in toluene. After 1 hour at −78° C., a solution of phenylselenylchloride (755 mg, 3.94 mmol) in 5 ml of anhydrous THF was added. The reaction mixture was allowed to warm to room temperature and stirred for 2 hours before quenching with 5 ml of saturated $NH_4Cl$. The mixture was partitioned between saturated $NH_4Cl$ and ethyl acetate. The organic layers were dried over $Na_2SO_4$ and concentrated under vacuum to afford 2.197 g of the subtitle compound as an orange oil.

C. Trans-dl-4-t-butyloxycarbonyl-8-chloro- 3,4,4a,5,6,10b-hexahydrobenzo[f]quinolin-3-one and trans-dl- 4-t-butyloxycarbonyl-8-chloro-2,3,4,4a,5,6-hexahydrobenzo[f]quinolin-3-one.

To a solution of the selenide prepared above in Step B (2.197 g, 4.48 mmol) in 20 ml of THF at 0° C. buffered with excess solid $NaHCO_3$ was added 1.2 equivalents of 30% hydrogen peroxide (610 mg) in 4 ml of THF. After 30 minutes, the reaction mixture was partitioned between water and ethyl acetate. The organic layer was washed with saturated $NaHCO_3$, dried over $Na_2SO_4$, and concentrated under vacuum to afford 645 mg of a mixture of olefins. Separation of the $\Delta^{1,2}$ olefin from the $\Delta^{10b,1}$ olefin was accomplished by column chromatography on $SiO_2$ with 2:1 mixture of hexanes/ethyl acetate. The $\Delta^{1,2}$ olefin was obtained as 293 mg of a white solid (Example 50A). The more polar $\Delta^{10,1}$ olefin isomer was obtained as 149 mg of a white solid (Example 50B).

D. Trans-dl-8-chloro-3,4,4a,5,6,10b-hexahydrobenzo[f]quinolin-3-one and dl-8-chloro-2,3,4,4a,5,6-hexahydrobenzo[f]quinolin-3-one.

To a solution of the protected $\Delta^{1,2}$ olefin obtained in Step C (290 mg, 0.869 mmol) in 20 ml of $CH_2Cl_2$ was added trifluroacetic acid (0.14 ml, 1.74 mmol). The reaction mixture was stirred at room temperature for one hour and then partitioned between $CH_2Cl_2$ and saturated $NaHCO_3$. The organic layer was dried over $Na_2SO_4$ and concentrated under vacuum. The crude product obtained was recrystallized from ethyl acetate to afford 142 mg (70%) of white crystalline trans-dl-8-chloro-3,4,4a,5,6,10b-hexahydrobenzo[f]quinolin-3-one (Example 50A). Melting point 227°–228° C.

| Elemental Analysis: | | | |
|---|---|---|---|
| | C | H | N |
| Calculated: | 66.81 | 5.18 | 5.99 |
| Found: | 67.09 | 5.18 | 6.22 |

The protected $\Delta^{1,10b}$ olefin (149 mg, 0.446 mmol) was treated in a similar manner as described above for the protected $\Delta^{1,2}$ olefin with the exception that the crude product was purified by column chromatography on $SiO_2$ (5% isopropanol/$CHCl_3$) to afford 65 mg (62%) of dl-S-chloro-2,3,4,4a,5,6 -hexahydrobenzo[f]quinolin-3-one (Example 50B) as a white solid. Melting point 241°–243° C.

| Elemental Analysis: | | | |
|---|---|---|---|
| | C | H | N |
| Calculated: | 66.81 | 5.18 | 5.99 |
| Found: | 67.06 | 5.35 | 5.93 |

EXAMPLE 51

Preparation of trans-dl-8-bromo-4-methyl- 3,4,4a,5,6,10b-hexahydrobenzo[f]quinolin-3-one.

Trans-dl-8-bromo-4-methyl-1,2,3,4,4a,5,6,10b-octahydrobenzo[f]quinolin-3-one was prepared according to the procedures described in Example 1. This compound was converted to the title compound according to the procedures described in Example 50, Steps B and C followed by recrystallization from ethyl acetate/hexanes. Melting point 136°–138° C.

| Elemental Analysis: | | | |
|---|---|---|---|
| | C | H | N |
| Calculated: | 57.55 | 4.83 | 4.79 |
| Found: | 57.81 | 4.74 | 4.81 |

EXAMPLE 52

Preparation of trans-dl-8-chloro-4-methyl- 3,4,4a,5,6,10b-hexahydrobenzo[f]quinolin-3-one.

Trans-dl-8-chloro-4-methyl-1,2,3,4,4a,5,6,10b-octahydrobenzo[f]quinolin-3-one was prepared according to the procedures described in Example 6. This compound was converted to the title compound according to the procedures described in Example 50, Steps B and C followed by column chromatography on $SiO_2$ (ethyl acetate). Melting point 124°– 125° C.

| Elemental Analysis: | | | |
|---|---|---|---|
| | C | H | N |
| Calculated: | 67.88 | 5.70 | 5.65 |
| Found: | 67.77 | 5.77 | 5.38 |

EXAMPLE 53

Preparation of dl-8-chloro-4-methyl-2,3,4,4a,5,6-hexahydrobenzo[f]quinolin-3-one.

Trans-dl-8-chloro-4-methyl-3,4,4a,5,6,10b-hexahydrobenzo[ f]quinolin-3-one was prepared according to the procedures described in Example 52. To this compound (250 mg, 1 mmol) in 30 ml of anhydrous THF was added 800 mg (6.8 mmol) of pyridine hydrochloride. The reaction mixture was stirred at room temperature for seven days and then partitioned between ethyl acetate and 1N HCl. The organic layer was washed with iN HCl followed by water then dried over MgSO$_4$ and concentrated under vacuum to 10 ml volume. The title compound was crystallized from this solution and was collected by filtration. Melting point 99° C.

Elemental Analysis:

|  | C | H | N |
|---|---|---|---|
| Calculated: | 68.16 | 5.31 | 5.67 |
| Found: | 67.95 | 5.48 | 5.64 |

EXAMPLE 54

Preparation of trans-dl-8-chloro-2-a-methyl-4 -methyl-1, 2,3,4,4a,10b-hexahydrobenzo[f]quinolin-3-one.

A mixture of trans-dl-8-chloro-2-(a and b)-methyl- 4-methyl-1,2,3,4,4a,5,6,10b-octahydrobenzo[f]quinolin-3-ones was prepared according to the procedure described in Example 26. To a solution of this mixture (759 mg, 2.88 mmol) at −78° C. in 15 ml of anhydrous THF in the presence of 2.0 equivalents of hexamethylphosphorictriamide (HMPA) was added 11.6 ml of a 0.5M solution of potassium hexamethyldisilazide (5.76 mmol) in toluene. The reaction mixture was stirred at −78° C. for ninety minutes before the addition of a solution of phenylselenyl chloride (607 mg, 3.17 mmol) in 5 ml of anhydrous THF. The solution was allowed to warm to room temperature over a 2 hour period, quenched with a saturated NH$_4$Cl solution and the mixture extracted with ethyl acetate. The combined organic layers were washed with saturated NH$_4$Cl, dried over Na$_2$SO$_4$, and concentrated under vacuum to afford 1.42 of a brown oil. The crude product was purified by column chromatography on SiO$_2$ (ethyl acetate) to give 252 mg of the 6-phenylselenide. To a solution of the selenide in 10 ml of THF was added 100 mg of NaHCO$_3$ and approximately 1.1 equivalent of 3-chloroperoxybenzoic acid (m-CPBA) (142 mg of 80–85% grade of m-CPBA, 658–700 mmol). After 15 minutes, the reaction mixture was partitioned between ethyl acetate and water. The aqueous layer was extracted with ethyl acetate and the combined organic layers were washed with saturated NaHCO$_3$ solution, dried over Na$_2$SO$_4$, and concentrated under vacuum. The crude oil so obtained was purified by flash chromatography on SiO$_2$ (70% ethyl acetate/hexanes) to afford 114 mg of the titled compound as a white solid. $^1$H-NMR analysis indicated that the $\Delta^{5,6}$ olefin had been formed and that the 2-methyl group was in the alpha orientation. Melting point 130°–132° C.

Elemental Analysis:

|  | C | H | N |
|---|---|---|---|
| Calculated: | 68.83 | 6.16 | 5.35 |
| Found: | 68.35 | 6.15 | 4.92 |

EXAMPLE 55

Preparation of trans-dl-8-t-butylaminocarbonylethanediyl- 4-methyl-1,2,3,4,4a,5,6,10b-octahydrobenzo-[f]quinolin-3-one.

The compound trans-dl-8-t-butylaminocarbonylethenediyl- 4-methyl-1,2,3,4,4a,5,6,10b-octahydrobenzo[ f]quinolin-3-one was prepared according to the procedures described in Example 25. To a solution of this compound (122 mg, 0.358 mmol) in 150 ml of anhydrous ethanol was added 15 mg of 10% palladium on carbon. The mixture was hydrogenated at room temperature for six hours under an initial hydrogen pressure of 40 p.s.i. The catalyst was removed by filtration through diatomaceous earth (Celite®) and the filtrate concentrated to give a white solid. Proton NMR spectroscopy indicated that the reaction was not complete, therefore, the material was resubmitted to the same reaction conditions for an additional 6 hours. Purification of the solid obtained was accomplished using column chromatography on SiO$_2$ (20% isopropanol/ethyl acetate) to afford the title compound as a white solid. Melting point 178°–179° C.

Elemental Analysis:

|  | C | H | N |
|---|---|---|---|
| Calculated: | 73.65 | 8.83 | 8.18 |
| Found: | 73.21 | 8.69 | 8.32 |

EXAMPLE 56

Preparation of trans-dl-8-phenyl-4-methyl- 1,2,3,4,4a,5,6, 10b-octahydrobenzo[f]quinolin-3-one.

The compound trans-dl-8-bromo-4-methyl- 1,2,3,4,4a,5, 6,10b-octahydrobenzo[f]quinolin-3-one was prepared according to the procedures described in Example 1. To a mixture of this compound (160 mg, 0.54 mmol) and tetrakistriphenylphosphine palladium (0) (19 mg, 0.02 mmol) in 1.2 ml of toluene under a nitrogen atmosphere was added 0.6 ml of a 2M solution of aqueous Na$_2$CO$_3$ followed by phenylboronic acid (80 mg, 0.653 mmol). The reaction mixture was heated at 80° C. for 18 hours. The mixture was allowed to cool and then partitioned between 75 ml of CH$_2$Cl$_2$ (75 ml) and 25 ml of 2M aqueous Na$_2$CO$_3$ with 2 ml of concentrated NH$_4$OH added. The organic layer was dried over MgSO$_4$ and concentrated to give a tan solid. The title compound (106 mg, 67%) as a white crystalline solid, was obtained after flash chromatoghraphy on SiO$_2$ (5% isopropanol/CHCl$_3$) and trituration of the product with hexane. Melting point 186.5°– 187.5° C.

Elemental Analysis:

|  | C | H | N |
|---|---|---|---|
| Calculated: | 82.44 | 7.26 | 4.81 |
| Found: | 82.38 | 7.12 | 5.08 |

EXAMPLE 57

Preparation of trans-dl-8-vinyl-4-methyl- 1,2,3,4,4a,5,6, 10b-octahydrobenzo[f]quinolin-3-one.

The compound trans-dl-8-bromo-4-methyl- 1,2,3,4,4a,5, 6,10b-octahydrobenzo[f]quinolin-3-one was prepared according to the procedures described in Example 1. To a sealable tube was added the 8-bromo benzoquinolinone (1.00 g, 3.4 mmol), palladium (II) acetate (7.6 mg, 0.034 mmol), tri-o-tolylphosphine (41 mg, 0.136 mmol), vinyltributyltin (1.24 ml, 4.25 mmol) and 5 ml of anhydrous dioxane. Argon was bubbled through the mixture for 15 minutes. The reaction tube was sealed and heated at 100° C. with stirring for 18 hours. The reaction mixture was cooled and filtered through diatomaceous earth Celite®. The filtrate was concentrated under vacuum and the resulting material was analyzed by capillary gas chromatography (G.C.) which revealed it to be a 4.7 to 1 mixture of the desired product to starting material. Column chromatography of this mixture on $SiO_2$ (7% methanol/$CHCl_3$) afforded the title compound as 212 mg of a white solid. Melting point 89°–90° C.

| | Elemental Analysis: | | |
|---|---|---|---|
| | C | H | N |
| Calculated: | 79.63 | 7.94 | 5.80 |
| Found: | 79.39 | 7.98 | 5.56 |

EXAMPLE 58

Preparation of trans-dl-8-ethoxycarbonyl-4-methyl- 1,2,3,4,4a,5,6,10b-octahydrobenzo[f]quinolin-3-one.

The compound trans-dl-8-iodo-4-methyl- 1,2,3,4,4a,5,6,10b-octahydrobenzo[f]quinolin-3-one was prepared according to the procedures described in Example 3. To a solution of the iodide (1.0034 g, 2.94 mmol) in 280 ml of ethanol was added tetrakistriphenylphosphine palladium (II) chloride (160 mg) and 1.0 ml of triethylamine. The mixture was purged with nitrogen for 30 minutes followed by purging with carbon monoxide. The reaction mixture was fitted with a CO balloon and refluxed for 48 hours. After filtration of the reaction mixture through diatomaceous earth, Celite®, the filtrate concentrated under vacuum to yield an orange vicous oil. Proton NMR spectroscopy revealed that the reaction was not complete. The oil was resubmitted to the conditions described above for an additional 48 hours. Capillary gas chromatography (G.C.). indicated the reaction was 85% complete. The resulting material was purified by column chromatography on $SiO_2$ (10% methanol/$CHCl_3$) followed by HPLC on a reversed phase CN column to afforded 122 mg of the title compound. Melting point 140°–140.5° C.

| | Elemental Analysis: | | |
|---|---|---|---|
| | C | H | N |
| Calculated: | 71.06 | 7.37 | 4.87 |
| Found: | 70.97 | 7.17 | 4.60 |

EXAMPLE 59

Preparation of (R)(+)-trans-4-methyl-8-chloro-10b-methyl- 1,2,3,4,4a,5,6,10b-octahydrobenzo[f]quinolin-3-one.

By following the procedures described in Example 40, Steps A, B, C, D, E and F using p-chlorophenylacetic acid as the starting material and in Step F using methylamine rather than ammonia and 2-propanol rather than ethylene glycol, the compound (R)(+)-4-methyl-8-chloro-10b-methyl- 1,2,3,4,6,10b-hexahydro-benzo[f]quinolin-3-one was prepared. This hexahydrobenzo[f]quinolin-3-one was reduced according to the procedure described in Example 40, Step G. The crude product was purified by chromatography on $SiO_2$ (ethyl acetate as eluent) to afford 5.6 g of the title compound as a pale oil which solidified on standing. Melting point 60°–61° C.

| | Elemental Analysis: | | |
|---|---|---|---|
| | C | H | N |
| Calculated: | 68.30 | 6.88 | 5.31 |
| Found: | 68.14 | 6.94 | 5.27 |

Optical rotation: 589 nm=+76.16° (C=1, $CHCl_3$)

EXAMPLE 60

Preparation of (R) (+)-trans-4-methyl-8-chloro-10b-methyl- 3,4,4a,5,6,10b-hexahydrobenzo[f]quinolin-3-one.

By following the procedures described in Example 59, the compound (R)(+)-trans-4-methyl-8-chloro-10b-methyl- 1,2,3,4,4a,5,6,10b-octahydrobenzo[f]quinolin-3-one was prepared as a mixture (4:1 trans:cis) with its cis isomer. A stirred, cooled (−78° C.) solution of 1.4 g (5.56 mmol) of this mixture in THF (25 mL) was treated with potassium hexamethyldisilazide (12.2 mL; 6.12 mmol) solution in toluene. The solution was stirred for 30 min. and treated with a solution of phenyl selenyl chloride (1.17 g; 6.117 mmol) in 5 mL of THF. The solution was warmed to ambient temperature over 1 hour and then quenched with 20 mL of saturated $NH_4Cl$ solution. The mixture was partitioned between ethyl acetate and water and the aqueous phase was dried over $Na_2SO_4$ and was concentrated to afford a diastereomeric mixture of phenyl selenides. The crude phenyl selenides were dissolved in 10 mL of ethyl acetate and cooled to 0° C. Saturated $NaHCO_3$ solution (2 mL) was added to the solution, followed by 0.4 mL of 30% $H_2O_2$. The mixture was warmed to ambient temperature and was stirred for 2 hours. The mixture was extracted with ethyl acetate and the residue chromatographed on $SiO_2$ (ethyl acetate as eluent) to afford 611 mg of the title compound as a waxy solid. Melting point 45°–48° C.

| | Elemental Analysis: | | |
|---|---|---|---|
| | C | H | N |
| Calculated: | 68.83 | 6.16 | 5.35 |
| Found: | 69.26 | 6.48 | 5.08 |

Optical rotation: 589 nm=+87.38° (C=1, $CHCl_3$)

EXAMPLE 61

Preparation of (R)(+)-trans-8-chloro-10b-methyl- 3,4,4a,5,6,10b-hexahydrobenzo[f]quinolin-3-one.

By following the procedures described in Example 40, Steps A, B, C, D, E, F, and G , the compound (R)(+)-8-chloro-10b-methyl-1,2,3,4,4a,5,6,10-octahydrobenzo[f]quinolin-3-one was prepared as a mixture (4:1) of trans and cis isomers. The mixture (1.02 g; 4.07 mmol) was dissolved in 15 mL of dioxane and treated with dichlorodicyanoquinone (1.02 g; 4.45 mmol) followed by bis(trimethylsilyl)trifluoroacetamide (4.8 mL; 17.9 mmol). The solution was stirred at ambient temperature for 4 hours and then was heated to 100° C. for 14 hours. The reaction mixture was cooled to ambient temperature and was partitioned between ethyl acetate and water. The organic phase was concentrated under vacuum and the residue chromatographed on $SiO_2$ (ethyl acetate as eluent) to afford 670 mg of the title compound as an oil. A sample was crystallized from diethyl ether to afford 60 mg of the title compound as a pale solid. Melting point 151°–154° C.

| Elemental Analysis: | | | |
|---|---|---|---|
| | C | H | N |
| Calculated (+½ mol H₂O) | 65.50 | 5.89 | 5.46 |
| Found: | 65.67 | 6.06 | 5.40 |

Optical rotation: 589 nm=+51.33°
(C=1, CHCl₃) 365 nm=−85.55°

EXAMPLE 62

Preparation of trans-dl-8-trifluoromethyl-4-methyl- 1,2,3,4,4a,5,6,10b-octahydrobenzo[f]quinolin-3-one.

Trans-dl-8-bromo-4-methyl-1,2,3,4,4a,5,6,10b-octahydrobenzo[ f]quinolin-3-one was prepared according to the procedures described in Example 1. A mixture of the bromide (1.2 g, 4.1 mmol), sodium trifluoroacetate (2.22 g, 16.3 mmol) and cuprous iodide (1.55 g, 8.1 mmol) in 25 ml of N-methyl- 2-pyrrolidinone were heated at 180° C. for 18 hours under an argon atmosphere. After cooling, the mixture was filtered through silica gel and the silica gel plug was washed with ethyl acetate. The combined organic layers were washed twice with water and once with brine, dried over MgSO₄, and evaporated under vacuum to afford 1.14 g of a black oil which crystallized on standing. The crude product was purified by flash chromatography on silica gel (ethyl acetate) followed by reverse phase chromatography (1:1 water/acetonitrile) to give 312 mg of a white solid (27% yield).

High Resolution mass spectrum. Calculated for C₁₅H₁₃F₃NO (283.118480); found 283.119620.

EXAMPLE 63

Preparation of (+)-(4aR)-(10bR)-8-chloro-1,2,3,4,4a,5,6,10b-octahydrobenzo[ f]quinolin-3-one A. (S)-(−)-8-chloro-4-(α-methylbenzyl)-1,2,3,4,5,6-hexahydrobenzo[f]quinolin-3-one

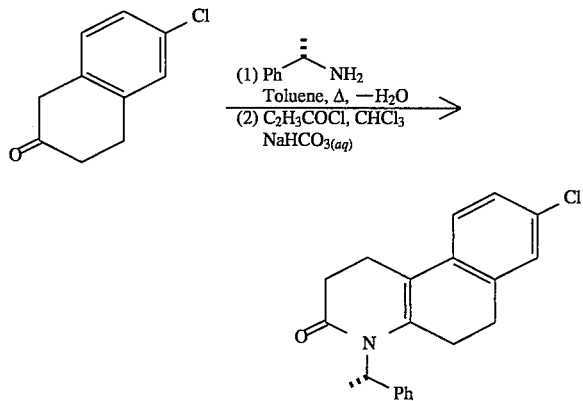

To a stirred solution of 6-chloro-2-tetralone (1.0 equiv., 100.0 mmol., 18.06 g) in toluene (300 ml) was added (S)-(−)-α-methylbenzylamine (1.0 equiv., 100.0 mmol., 12.9 ml). The mixture was heated at reflux for 3 hrs with the azeotropic removal of water (Dean-Stark). The cooled reaction mixture was concentrated in vacuo to give the enamine, (S)-6-chloro-2-(α-methylbenzyl)-3,4-dihydronaphthalene, as a purple oil. The oil was taken up in chloroform (150 ml) and saturated aqueous sodium bicarbonate was added (150 ml). The vigorously stirred mixture was treated with acryloyl chloride (1.05 equiv., 105.0 mmol., 8.5 ml) dropwise over 5 min. The reaction mixture was allowed to stir at ambient temperature for 20 min., then diluted with chloroform and the layers separated. The aqueous layer was extracted with chloroform (1×). The combined organics were washed with brine (1×), dried (Na₂SO₄), and concentrated in vacuo to give 37.9 g of a black oil. The crude oil was subjected to HPLC on silica gel (gradient elution with hexanes increasing to 25% ethyl acetate/hexanes) to give 19.03 g of a purple oil which was further purified by flash chromatography on silica gel (elution with 20% ethyl acetate/hexanes) to give 17.96 g, 53% yield of the title compound as a brown glass which was homogeneous by HPLC analysis (reverse phase, C₁₈, mobile phase: 60% acetonitrile/0.5% aqueous ammonium acetate buffer),thin layer chromatography (Silica gel, R_f=−0.5, developed with 40% ethyl acetate/hexanes), and 300 MHz ¹H NMR analysis. FDMS: m/e=337. α[D]₅₈₉=−24.75 (c=1.0, CHCl₃).

B. (−)-(4aR)-(10bR)-8-chloro-4-(S-α-methylbenzyl)- 1,2,3,4,4a,5,6,10b-octahydrobenzo[ f]quinolin-3-one

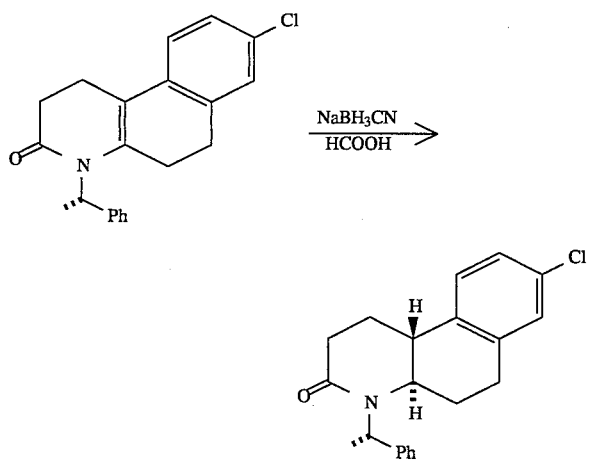

A stirred solution (12.0 g; 35.4 mmol) of the product of Step A in 96% formic acid (175 ml) was treated with solid sodium cyanoborohydride (2.0 equiv., 70.98 mmol., 4.46 g) every hr for 5 hrs (total of 10 equiv., 354.9 mmol., 22.3 g). The mixture was allowed to stir overnight (ca. 14 hrs) at ambient temperature. The reaction mixture was concentrated in vacuo to give a pale yellow paste which was taken up in dichloromethane and washed with 1N sodium hydroxide (1×). The aqueous layer was back extracted with dichloromethane (2×). The combined organics were washed with brine (1×), dried (Na₂SO₄), and concentrated in vacuo to give 12.0 g of a colorless foam. Preparative HPLC of the residue on silica gel (gradient elution dichloromethane-1% ethyl acetate/dichloromethane) and combination of the fractions that were greater than 90% diastereomerically pure gave 1.63 g of the title compound as a crystalline solid (HPLC analysis: reverse phase, C₁₈, 230 nm, mobile phase: 60% acetonitrile/40% 0.5% ammonium acetate buffer). Recrystallization of the solid from ethyl acetate gave the title compound in diastereomerically pure form as colorless needles (greater than 99:1 diastereomeric purity, HPLC analysis). The fractions that were enriched with the title compound were combined and concentrated in vacuo to give 3.0 g of a colorless foam. Fractional crystallization of this material from ethyl acetate (3 crystallizations) gave an additional 870 mg of pure title compound, 2.50 g, 21% yield. mp 176°–177° FDMS: m/e=339. α[D]$_{589}$=–126.63 (c=1.0, CHCl$_3$). The absolute configuration of the title compound was elucidated by a single crystal x-ray diffraction study.

|   | Theory | Found |
|---|--------|-------|
| C | 74.21  | 74.07 |
| H | 6.52   | 6.59  |
| N | 4.12   | 4.04  |

C. (+)-(4aR)-(10bR)-8-chloro-1,2,3,4,4a,5,6,10b-octahydroenzo[f]quinolin-3-one

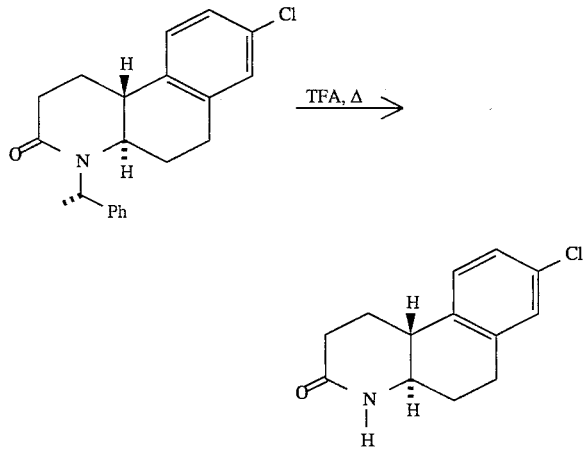

A mixture of the product of Step B (1.0 equiv., 4.09 mmol., 1.39 g) and trifluoroacetic acid (35 ml) were combined in a round bottom flask. The stirred mixture was heated at reflux for 2 hrs. The cooled reaction mixture was concentrated in vacuo, taken up in dichloromethane and washed with a saturated aqueous solution of sodium bicarbonate (1×). The layers were separated and the aqueous layer was back extracted with dichloromethane (1×). The combined organics were washed with brine (1×), dried (Na$_2$SO$_4$), and concentrated in vacuo to give a white solid. Recrystallization from ethyl acetate gave 0.81 g, 84% yield of the title compound as colorless needles. mp 241.5°–242°. FDMS: m/e=235. α[D]$_{589}$ =32.61 (c=1.0, THF).

|   | Theory | Found |
|---|--------|-------|
| C | 66.24  | 66.35 |
| H | 5.99   | 6.10  |
| N | 5.94   | 5.83  |

EXAMPLE 64

(–)-(4aR)-(10bR)-8-chloro-1-methyl-1,2,3,4,4a,5,6,10b-octahydrobenzo[f]quinolin-3-one

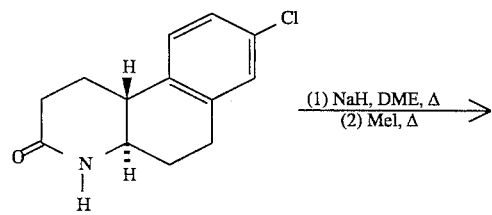

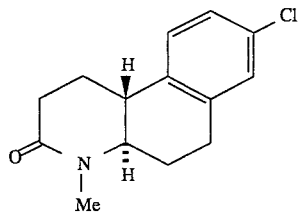

To a stirred solution of the product of Step C, Example 63 (1.0 equiv., 0.288 mmol., 98 mg) in dry 1,2-dimethoxyethane (5 ml) was added a 60% (w/w) oil dispersion of sodium hydride (26 mg). The mixture was heated at reflux under a nitrogen atmosphere with stirring for 1 hr, cooled and treated with methyl iodide (5.0 equiv., 1.44 mmol., 0.09 ml). The mixture was refluxed an additional 1.5 hrs. The cooled reaction mixture was quenched with water (1 ml) and extracted with dichloromethane (3×). The combined organics were washed with brine (1×), dried (Na$_2$SO$_4$), and concentrated in vacuo to give an orange oil. Preparative thin layer chromatography on silica gel (2 mm plate, developed with ethyl acetate) gave 50 mg, 69% yield as a colorless solid. mp 71.5°–73°. α[D]$_{589}$=–74.80 (c=1.0, CHCl$_3$). HRMS (FAB+) Calculated for C$_{14}$H$_{17}$NOCl: 250.1003. Observed 250.0999.

EXAMPLE 65

Preparation of (+)-(4aS)-(10bS)-8-chloro-4-(methyl)-1,2,3,4,4a,5,6,10b-octahydrobenzo[f]quinolin-3-one A. (+)-(4aS)-(10bS)-8-chloro-4-(S-α-methylbenzyl)-1,2,3,4,4a,5,6,10b-octahydrobenzo[f]quinolin-3-one

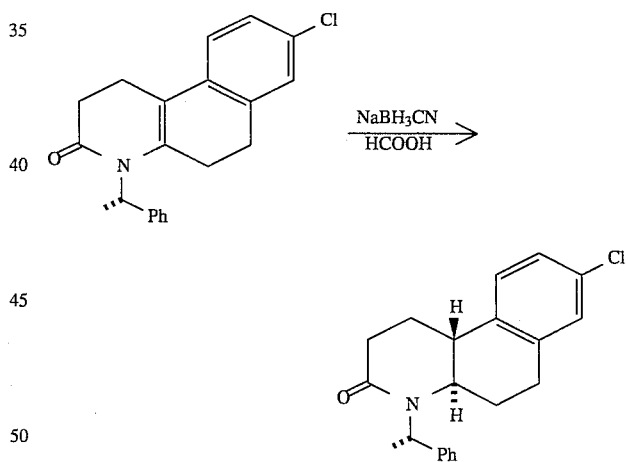

A stirred solution of the product of Step A, Example 63 in 96% formic acid (20 ml) was treated with sodium cyanoborohydride in portions over 8 hrs (30 equiv., 88.8 mmol., 5.58 g at ambient temperature. The mixture was then heated at 50° for 2 hrs. The cooled reaction mixture was concentrated in vacuo to give a colorless foam. The residue was taken up in dichloromethane and washed with water (1×). The aqueous layer was back extracted with dichloromethane (2×). The combined organics were washed with 1N sodium hydroxide (1×), brine (1×), dried (Na$_2$SO$_4$), and concentrated in vacuo to give a colorless foam. Medium pressure liquid chromatography on silica gel (elution with 10% ethyl acetate/dichloromethane) gave 201 mg of the product of Step B, Example 63. Further elution gave 129 mg of the title compound as a colorless solid, 13% yield. HPLC analysis of this material (reverse phase, $C_{18}$, 230 nm, 60% acetonitrile/40% 0.5% aqueous ammonium acetate buffer) revealed that the material was greater than 99% diastereomerically pure.

B. (+)-(4aS)-(10bS)-8-chloro-4-methyl -t, 2,3,4,4a,5,6,10 b-octahydrobenzo[f]quinolin-3-one

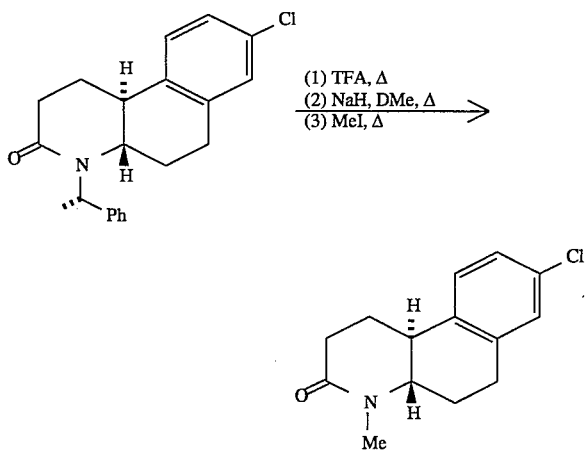

A stirred solution of the product of Step A (1.0 equiv., 0.359 mmol., 122 mg) in trifluoroacetic acid (6 ml) was heated at reflux for 1.5 hrs. The cooled reaction mixture was concentrated in vacuo to give a yellow solid which was taken up in dichloromethane and washed with a saturated solution of sodium carbonate (1×). The aqueous layer was back extracted with dichloromethane (1×). The combined organics were washed with brine (1×), dried (NaSO$_4$), and concentrated in vacuo to give (−)-(4aS)-(10bS)-8-chloro-1,2,3,4,4a,5,6,10b-octahydrobenzo[f]quinoline-3-one as a pale yellow solid. The residue was dissolved in dry 1,2-dimethoxyethane (5 ml) and treated with sodium hydride (19 mg, 60% dispersion in mineral oil washed 3× with pentane). The mixture was heated at reflux for 1.5 hrs, cooled and treated with methyl iodide (5.0 equiv., 1.80 mmol., 0.2 ml). The reaction mixture was heated an additional 1.5 hrs. The cooled reaction mixture was quenched with water, and extracted with dichloromethane (3×). The combined organics were washed with brine (1×), dried (Na$_2$SO$_4$), and concentrated in vacuo to give an orange oil. Preparative thin layer chromatography on silica gel (2 mm plate, developed with ethyl acetate) gave the title compound (56 mg, 62% yield) as a colorless solid. mp 71.5°–73° . $\alpha[D]_{589}$=+79.00 (c=1.0, CHCl$_3$). HRMS (FAB+): Calculated for $C_{14}H_{17}NOCl$: 250.0999. Observed 250.1002.

The following abbreviations are used in Examples 66 through 69

"HPLC SYSTEM A": 40% acetonitrile in water and 0.5% ammonium acetate on a Waters Nova-Pak C-8®, at 220 nm, at 2.00 mL/min, 25° C.

"HPLC SYSTEM B": 50% acetonitrile in water and 0.5% ammonium acetate on DuPont Zorbax ®C-18, at 220 nm, at 2.00 mL/min, 25 ° C.

"HPLC SYSTEM C": 10% isopropyl alcohol in hexane on a Chiralcel OD® at 254 nm at 1.00 mL/min and 25° C.

"HPLC SYSTEM D": 10% isopropyl alcohol in hexane on a Chiralcel OD® at 220 nm at 2.00 mL/min and 40° C.

EXAMPLE 66

Preparation of (+)-(4aR)-(10bR)-4-methyl-8-chloro- 5 1,2,3,4,4a,5,6,10b-octahydrobenzo[f]quinolin-3-one

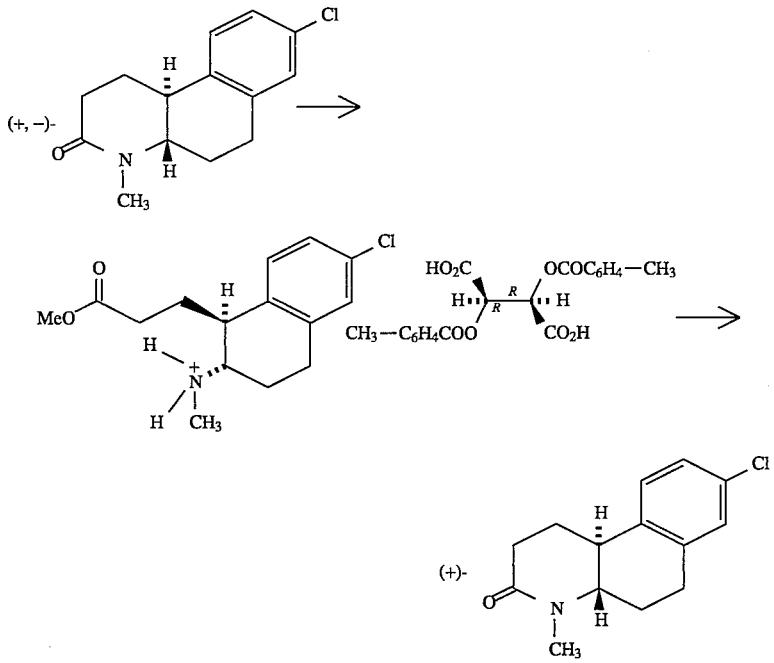

A. di-p-toluoyltartaric acid salt of 1-(2-methoxycarbonylethyl)- 2-(methylamino)-6-chloro-1,2,3,4 -tetrahydronaphthalene A solution of trans (d,l)-4-methyl-8-chloro- 1,2,3,4,4a,5, 6,10b-octahydrobenzo[f]quinolin-3-one (1.5 g) prepared substantially according to Example 6 in methanol (30 mL) with concentrated sulfuric acid (3.5 g) was refluxed for 144 hours. The solution was concentrated to approximately 20 ml and diluted with ether (50 mL), water (100 mL), and saturated sodium bicarbonate (20 mL, pH=9). The phases were separated and the aqueous phase further extracted with ethyl acetate (100 mL) and methylene chloride (100 mL). The combined organic phases were dried with 4-A molecular sieves and added to a solution of (−)-p-toluoyl-L-tartaric acid (DTTA) monohydrate (2.00 g) in methanol (10 mL). All volatiles were removed under vacuum and the resulting foam digested in approximately 40 mL of methanol. The solids were filtered and dried affording 1.01 g (50% of theory) of the salt admixed with 6.3% of non-hydrolyzed trans-dl-8-chloro-4 -methyl-1,2,3,4,4a,5,6,10b-octahydrobenzo[f]quinolin-3-one. m.p. 126°–130° C.

TLC (Silica gel with toluene-ethyl acetate-acetic acid-methanol 7:4:1:4): Rf=0.34 (phosphomolybdic acid visualization).

HPLC (SYSTEM A): tr (min): 0.48(43%, DTTA), tr=1.33(53%. free amino ester), $t_r$=3.36 (3.15%, racemate).

HPLC (SYSTEM B): tr(min) 1.06 (48.1%, DTTA), 2.77 (1.2%, unknown), 3.73 (46.1%, free amino ester), 5.54 (4.5%, (title compound).

$^1$H NMR (CDCl$_3$): δ 5.43 (s, 2H), 3.57 (s, 3H), 2.38 (s, 6H).

UV (methanol): λ(ε): 276 (30,100) .

IR (CHCl$_3$): 1723 cm$^{-1}$.

B. (+)-(4aR)-(10bR)-4-methyl-8-chloro-1,2,3,4,4a,5,6,10b-octahydrobenzo[ f]quinolin-3-one A solution of the above DTTA salt (100 mg) was stirred with toluene (5 mL), water (10 mL) and sodium bicarbonate (50 mL) for 20 minutes at 25° C. The toluene layer was separated, dried (sodium sulfate), heated (90°–100° C., 18 hours), and evaporated affording the title compound.

$^1$H NMR (Benzene-d$_6$): 6.99 (dxd, 1H) , 6.83 (d, 1H) , 6.57 (d, 1H), 2.67 (3H, s), 2.40 (dxt, 2H).

$^1$H NMR (Benzene-d$_6$ with 2 equiv R-(−)-2,2,2-trifluoro-1-(9-anthryl)ethanol (TFAE): d 2.14 (3H, s), Displayed upfield methyl singlet at 2.10 for 5–6% (−) enantiomer.

HPLC (SYSTEM A): $t_r$(min) 3.36 (title compound).

HPLC (SYSTEM B): $t_r$(min) 5.68 (title compound).

HPLC (SYSTEM D): $t_r$(min) 13.85 (92%, title compound), 15.8 (8%, (−)enantiomer) .

$^1$H NMR (CDCl$_3$): 3.07 (3 H, s).

EXAMPLE 67

Preparation of (+)-(4aR)-(10bR)-4-methyl-8-chloro- 1,2, 3,4,4a,5,6,10b-octahydrobenzo[f]quinolin-3-one

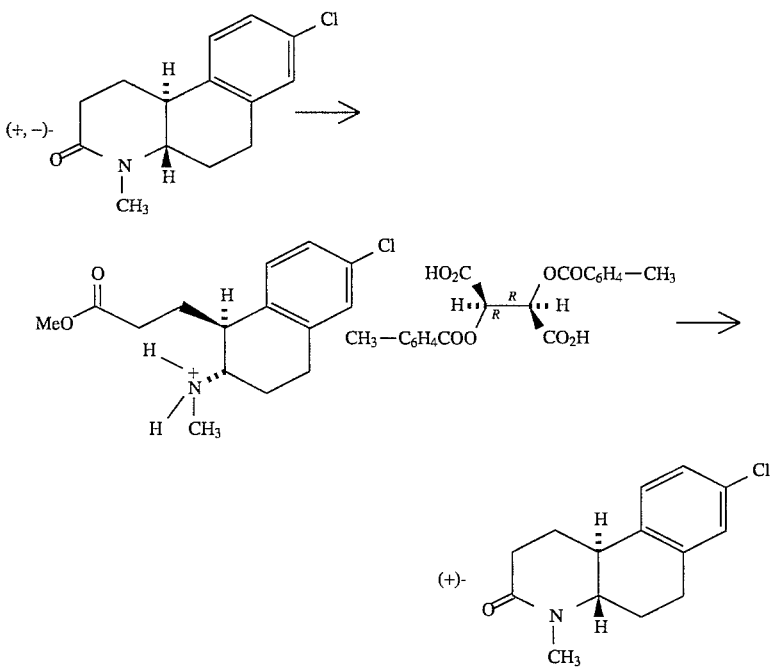

A. di-p-toluoyltartaric acid salt of 1-(2 -methoxycarbonylethyl)-2-(methylamino)-6-chloro-1,2,3,4-tetrahydronaphthalene A solution of trans-d,l-8-chloro-4-methyl-1,2,3,4,4a,5,6, 10b-octahydrobenzo[ f]quinolin-3-one (2.3 g) in 0.85N hydrochloric acid in methanol was allowed to reflux for 168 hours after which, concentrated sulfuric acid (3.00 mL) and additional methanol (100 mL) were added. After 96 hours, the mixture was concentrated and treated with solid sodium bicarbonate (20 g). The mixture containing 1-(2 -methoxycarbonylethyl)-2-(methylamino)-6-chloro-1,2,3,4-tetrahydronaphthalene was partitioned with ethyl acetate (100 mL) and water (100 mL). The phases were separated and the water layer extracted with 250 mL of of methylene chloride. The organic phases were combined and filtered over 3-A molecular sieves (15 g) into a solution of 5.9 g of (−)-p-toluoyl-L-tartaric acid monohydrate in methanol. All volatiles were removed under vacuum and the white foam dried under vacuum for 30 hours affording the diastereomeric salt (6.1 g, 99%, containing 5.0% of non-hydrolyzed, trans-dl-8 -chloro-4-methyl-1,2,3,4,4a,5,6,10b-octahydrobenzo[f] quinolin- 3-one) m.p. 126°–130° C.

The above foam (DTTA salt) (5.69 g) was digested in methanol (43° C., 32 mL) and the resulting solution cooled to 25° C. The mixture was filtered and vacuum dried affording 2.92 g of DTTA salt. Recrystallization of this salt (2.28 g) from 30 mL of methanol gave 2.12 g of constitutionally pure salt (47%, 94% of theory).

HPLC (SYSTEM A): 0.48 (46%, DTTA), 1.28 (.54%, amino ester), no other impurities detected.

B.  (+)-(4aR)-(10bR)-4-methyl-8-chloro-1,2,3,4,4a,5,6,10b-octahydrobenzo[f]quinolin-3-one The salt from above (1.50 g) was stirred (25° C., 10 minutes) with toluene (30 mL), saturated aqueous sodium bicarbonate (10 mL) and water (40 mL). The phases were separated and the toluene layer was dried (3-A molecular sieves). The resulting solution was heated (16 hours, 92° C.) and evaporated affording 0.55 g of (+)-(4aR)-(10bR)-4-methyl-8 -chloro-1,2,3,4,4a,5,6,10b-octahydrobenzo[f]quinolin-3-one admixed with 5–7% of the enantiomer (–)-(4aR)-(10bR)-8 -chloro-4-methyl-1,2,3,4,4a,5,6,10b-octahydrobenzo[f]quinolin- 3-one.

HPLC (SYSTEM A): 3.36 (97.9%, title compound).

HPLC (SYSTEM B): 5.76 (99.9%, title compound).

HPLC (SYSTEM C): 93% title compound and 7% (–)enantiomer.

UV (methanol) 204 (24100).

EXAMPLE 68

Preparation of (–)-(4aR)-(10bR)-8-chloro-4-methyl- 1,2,3,4,4a,5,6,10b-octahydrobenzo[f]quinolin-3-one.

tartaric acid (DTTA) monohydrate (derived from unnatural tartaric acid (S,S isomer), 132.9 g) in methanol (700 mL) and three crystallizations gave 48.2 g of the purified salt (m.p. 125°– 130° C. suitable for an analytical standard).

HPLC (SYSTEM A): 0.48 (DTTA) , 1.28 (amino ester) .

UV (methanol): 204 (51200), 239 (31400), 270 (2500).

B.   (–)-(4aR)-(10bR)-8-chloro-4-methyl-1,2,3,4,4a,5,6,10b-octahydrobenzo[f]quinolin-3-one.

The DTTA salt from above (500 mg) was stirred with 10 mL of toluene, 5 mL of water, and 5 mL of saturated aqueous sodium bicarbonate (25° C.). The aqueous layer was separated and extracted again with toluene (5 mL). The combined toluene extracts were washed once with saturated sodium bicarbonate (5 mL), dried (4-A molecular sieves), and heated at 95°–105° C. (18 hours). The toluene was removed in a stream of nitrogen at 40° C. and the resulting oil triturated with hexane-ether affording the subtitled compound.

TLC (Silica gel with toluene-ethyl acetate-acetic acid, 7:4:1): $R_f$=0.68.

HPLC (SYSTEM A): 3.25 min (>99%, title compound)

HPLC (SYSTEM C): 31.12 min (>99% title compound), 28 min (<1% (+) enantiomer).

$^1$H NMR (CDCl$_3$): 3.22 (dxd).

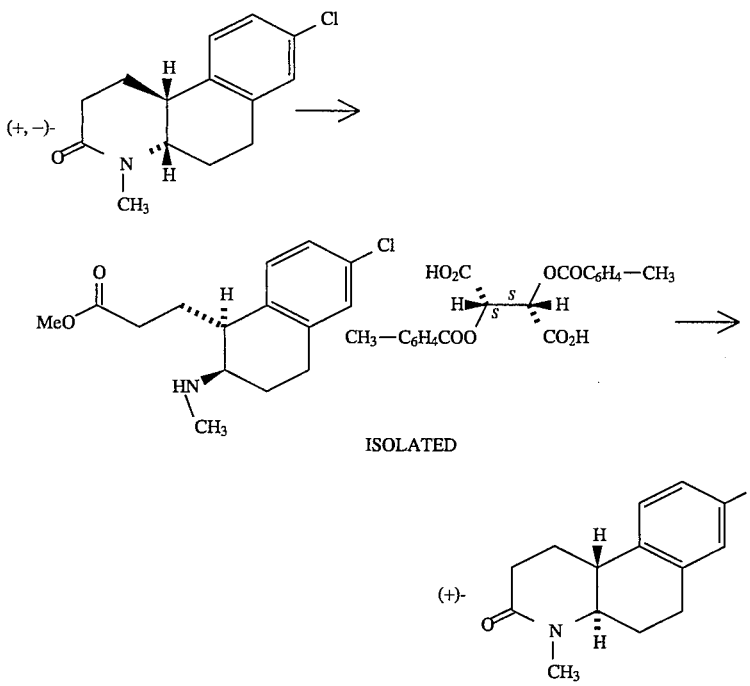

A. di-p-toluoyltartaric acid salt of 1-(2 -methoxycarbonylethyl)-2-(methylamino)-6-chloro-1,2,3,4-tetrahydronaphthalene A solution of 90.0 g trans-dl-8-chloro-4-methyl- 1,2,3,4,4a,5,6,10b-octahydrobenzo[f]quinolin-3-one (approx. 95% purity by HPLC analysis) prepared substantially according to the procedures of Example 6, was stirred at reflux under nitrogen in anhydrous methanol (4 L) and sulfuric acid (98%, 200.0 mL) for 160 hours (<1.5% trans-dl-8-chloro-4-methyl- 1,2,3,4,4a,5,6,10b-octahydrobenzo[f]quinolin-3-one remaining by HPLC). The solution was concentrated under vacuum and extracted at 10°–15° C. using methylene chloride, sodium bicarbonate (700 g), and water (2 L). Treatment of the organic extracts with (+)-p-toluoyl-D-

IR (CHCl$_3$): 1620 cm$^{-1}$

UV (methanol): 205 (20800).

EXAMPLE 69

Preparation of di-p-toluoyltartaric acid salt of 1-(2 -methoxycarbonylethyl)-2-(methylamine)-6-chloro-1,2,3,4-tetrahydronaphthalene

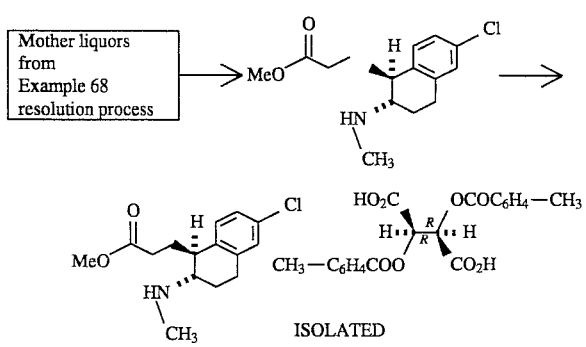

ISOLATED

The initial resolution-isolation filtrates and the mother liquor from the first recrystallization from Example 68 above were combined and evaporated at 25° C. under vacuum affording a white foam (190.4 g). This salt (180.4 g) was extracted with cold methylene chloride, water, sodium bicarbonate as described in Example 68. Treatment of the extracts with (−)-p-toluoyl-L-tartaric acid monohydrate (92.7g) in methanol. (450 mL) and three cystallizations gave pure DTTA salt (57.0 g). (mp 126°–13020 C.)

HPLC (SYSTEM A): 0.48 min (47%, DTTA), 1.28 (53%, amino ester).

IR (CHCl$_3$): 1720 cm$^{-1}$

UV (methanol): 204 (46200), 239 (28000), 270(4200).

By substantially following the procedures described above one skilled in the art can prepare the compounds of Formula I.

As noted above, the compounds of the present invention are useful for inhibiting the conversion of testosterone to 5α-dihydrotestosterone (DHT), and more particularly the type 1 isozyme. Therefore, another embodiment of the present invention is a method for inhibiting 5α-reductase by administering to a mammal in need of 5α-reductase inhibition a 5α-reductase inhibiting dose (effective amount) of a compound according to Formula I or a pharmaceutically acceptable salt thereof. The compounds of the present invention are useful alone, or in combination with other 5α-reductase inhibitors, particularly type 2 isozyme inhibitors, such as finasteride, 3-carboxy steroids described in Holt et al., *J. Med, Chem.* 33, 943–950 (1990) incorporated herein by reference, and the compounds disclosed in EP 0 291 245 also incorporated herein by reference.

The term "effective amount" as used herein, means an amount of a compound of the present invention which is capable of inhibiting the conversion of testosterone to 5α-dihydrotestosterone which is catalyzed by the enzyme 5α-reductase and particularly, inhibiting 5α-reductase; and more particularly the type I isozyme. The 5α-reductase inhibition contemplated by the present method includes both medical therapeutic and/or prophylactic treatment, as appropriate. The specific dose of compound administered according to this invention to obtain therapeutic and/or prophylactic effects will, of course, be determined by the particular circumstances surrounding the case, including, for example, the compound administered, the route of administration, and the condition being treated. A typical daily dose will contain a nontoxic dosage level of from about 0.01 mg/kg to about 50 mg/kg of body weight of the active compound of this invention. Preferred daily doses generally will be from about 0.05 to about 20 mg/kg and ideally from about 0.1 to about 10 mg/kg.

A variety of physiologic functions have been associated with the overproduction 5α-dihydrotestosterone. As such, the compounds of this invention are believed to have the ability to treat in mammals a variety of disorders associated with 5α-dihydrotestosterone including benign prostatic hyperplasia (or hypertrophy), male pattern baldness, ache vulgaris, seborrhea, androgenic alopecia, hirsutism and prostatic cancer. Therefore, the present invention also provides methods of treating the above disorders at the rates set forth above for inhibiting the 5α-reductase catalyzed conversion of testosterone to 5α-dihydrotestosterone. The compounds of the present invention are used alone, or in combination with other 5α-reductase inhibitors, particularly type 2 isozyme inhibitors, such as finasteride, the 3-carboxysteroids and compounds in EP 0 291 245, in these methods of treatment.

The compounds can be administered by a variety of routes including oral, rectal, transdermal, subcutaneous, intravenous, intramuscular, intranasal, and topical for male pattern baldness, acne vulgaris, and hirsutism. The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like. Typical formulations designed for topical administration are ointments, creams, gels, and lotions containing, for example, up to 10% by weight of the active compound.

The following formulation examples are illustrative only and are not intended to limit the scope of the invention in any way. "Active ingredient," of course, means a compound according to Formula I or a pharmaceutically acceptable salt thereof.

Formulation 1

Hard gelatin capsules are prepared using the following ingredients:

|  | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

|  | Quantity (mg/calpsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

|  | Weight |
| --- | --- |
| Active ingredient | 0.25 |
| Ethanol | 25.75 |
| Propellant 22 | 70.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are %hen added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
| --- | --- |
| Isotonic saline | 1,000 ml |

The solution of the above ingredients generally is administered intravenously to a subject at a rate of 1 ml per minute.

Ointments generally are prepared using either (1) an oleaginous base, i.e., one consisting of fixed oils or hydrocarbons, such as white petrolatum or mineral oil, or (2) an absorbant base, i.e., one consisting of an anhydrous substance or substances which can absorb water, for example, anhydrous lanolin. Customarily, following formation of the base, whether oleaginous or absorbent, the active ingredient is added in an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient customarily is added in an amount to achieve the desired concentration.

Gels comprise a base selected from an oleaginous base, water, or an emulsion-suspension base, such as described above. To the base is added a gelling agent which forms a matrix in the base, increasing its viscosity. Examples of gelling agents are hydroxypropyl cellulose, acrylic acid polymers, and the like. Customarily, the active ingredient is added to the formulation at the desired concentration at a point preceding addition of the gelling agent.

The amount of active ingredient incorporated into the formulation of this invention is not critical; the concentration should only be in a range sufficient to permit ready application of the formulation to the area of administration in an amount which will deliver the desired amount of active ingredient.

The following experiments were carried out to demonstrate the ability of the compounds of the present invention to inhibit 5α-reductase.

Cell Culture: 5α-Reductase activity was measured using Hs68 human genital skin fibroblasts which were originally purchased from the American Type Culture Collection (Rockville, Md.). The cells were grown in Dulbecco's Modified Eagle's Medium (DMEM) plus 10% stripped fetal bovine serum which was supplemented with amphotericin B (0.25 mg/ml) and gentamicin (25.0 mg/ml) (GIBCO, Grand Island, N.Y.). The serum was stripped of endogenous steroids by incubation with dextran-coated charcoal prior to its addition to the media. The cells were maintained at 37° C. in an atmosphere of 95% air, 5% $CO_2$ and were passaged every 7–10 days by exposure to a trypsin-EDTA solution (0.025% trypsin, 0.265 mM EDTA). Prior to the assay the Hs68 cells were harvested and plated in Falcon 6-well plates (Becton Dickinson Labware, Lincoln Park, N.J.) at a density of $6 \times 10^4$ cells per well. The cells were allowed to grow for 4–5 days or until they reached approximately 80% confluence.

Assay Method I: The substrate was prepared by dissolving unlabeled testosterone (Sigma Chemical Co., Louis, Mo.) in absolute ethanol followed by the addition of [7-$^3$H (N)]-testosterone (23.3 Ci/mmole, New England Nuclear, Boston, Mass.). The steroid solution was taken to dryness under a stream of nitrogen and then reconstituted in media.

Assay Method II: The substrate used for this method was [$^{14}$C]-testosterone (50 mCi/mmol) (New England Nuclear, Boston, Mass.). An aliquot of the substrate was taken to dryness under a stream of nitrogen. After the addition of 30 μl of ethanol, the testosterone was dissolved in an appropriate volume of media.

Sample Preparation: The test compounds were brought up in absolute ethanol in order to achieve the desired concentration. Subsequent dilutions of the test compounds with media were performed by the Biomek 1000 Automated Laboratory Workstation (Beckman Instruments, Palo Alto, Calif.). The existing media in the sample wells was aspirated and replaced with fresh media. Test compound was then added to the wells followed by the addition of 0.5 ml of substrate. The volume of the incubation mixture was maintained at 2.0 ml. The final substrate concentration was 12 μM. The concentration of the test compounds ranged from 0.001–150 μM. An additional three wells (background) containing media and substrate but no cells were also included to account for the non-enzymatic metabolism of the substrate. The plates were returned to the incubator and incubated for four hours.

At the end of the incubation the media was collected and transferred to an extraction tube containing 5 ml of toluene-ethanol (9:1), to which has been added 20–250 μg each of unlabeled carrier steroids (estriol, estradiol, estrone, 5α-androstan-3α,17β-diol, 5α-androstan-3β,17β-diol, 4-androstene-3,17-dione, 5α-androstan-3,17-dione, testosterone, and 5α-dihydrotestosterone) (Steraloids, Inc., Wilton, N.H.). In the case of Assay Method I the extraction tube also contained 1,000 and 10,000 dpm of [4-$^{14}$C]-dihydrotestosterone (50–60 mCi/mmol) and [4-$^{14}$C]-testosterone (50 mCi/mmol) (New England Nuclear, Boston, Mass.), respectively. The [14C]-steroids were included as recovery standards to quantify procedural losses. A small amount of NaCl was also added to the extraction tubes to prevent foaming. The samples were vortexed for approximately 30 seconds and then centrifuged for 10 minutes at 500×g. The organic phase was collected and the samples taken to dryness, redissolved in dichloromethane-methanol (9:1) and were analyzed by thin layer chromatography using one of the methods described below.

Chromatography Method I (two-dimensional): The extracted samples were applied to silica gel 60$F_{254}$, 0.25 mm thick, thin layer chromatography plates (EM Science, Cincinnati, Ohio). The plates were developed in the first dimension with a solvent system containing dichloromethane-ethyl acetate-methanol-acetic acid (160:38:1.5:0.5, Mallinckrodt Inc., Paris, Ky.). The plates were removed from the tanks and allowed to dry before they were developed in the second dimension in a solvent system containing dichloromethane-methanol-ammonium hydroxide (180:19:1, Mallinckrodt Inc., Paris, Ky.).

Chromatography Method II (one-dimensional): The extracted samples were applied to silica gel 60$F_{254}$, 0.25 mm thick, thin layer chromatography plates (EM Science, Cincinnati, Ohio). The plates were developed in a solvent system containing either cyclohexane-ethyl acetate (1:1, Mallinckrodt Inc., Paris, Ky.) or chloroform-ethyl acetate (3:1, Mallinckrodt Inc., Paris, Ky.). Both of these solvent systems gave adequate separation and enabled a greater throughput when compared to the two-dimensional system described above.

The plates were initially viewed under 254 mm UV light and the visible spots marked. The plates were then sprayed with primulin (Aldrich Chemical Co., Milwaukee, Wis.) (0.001% in acetone-water (4:1)) according to the method of Wright, R. S., "A reagent for the non-destructive localization of steroids and some other lipophilic materials on silica gel thin-layer chromatograms," *J. Chromatogr.*, 59; 220–221 (1971) which allowed the identification of additional steroids under 365 mm UV light. Samples derived using Assay Method II were analyzed directly using the Ambis Radioanalytic Imaging System (Ambis Systems, Inc., San Diego, Calif.). In the case of samples run using Assay Method I, the spots were scraped from the plate using a glass wool plugged Pasteur piper attached to a vacuum line. The steroids were eluted directly into scintillation vials by the addition of 0.2 ml of dichloromethane followed by two washes of 2.0 ml of methanol. The organic solvent was evaporated, and 10.0 ml of scintillation fluid (Ready Organic, Beckman Instruments, Inc. Fullerton, Calif.) were added. Samples were analyzed by liquid scintillation spectrometry.

Following removal of the media for extraction, the cells were washed with phosphate buffered saline (PBS, pH 7.4), and then harvested by exposure to a trypsin-EDTA solution (0.025% trypsin, 0.265 mM EDTA). The cells were collected and centrifuged at 1400×g for 5 minutes. The supernatant was decanted and the cells were resuspended in PBS. An aliquot of the cell suspension was counted in a Coulter Counter Model ZM (Coulter Electronics, Ltd., Luton Beds, England). The remaining cells were sonicated and the protein was determined according to the method of Bradford, M. M., "A rapid and sensitive method for protein quantitation of microgram quantities of protein utilizing the principle of protein-dye binding," *Anal Biochem.*, 72; 248–254 (1976). Corrections were made for procedural losses, and the data were expressed as percent inhibition based on either steroid concentration in terms of picomoles per mg/protein or picomoles/$10^5$ cells.

Evaluation results are given in Table I. Percent inhibition is used on a scale of 0–100 percent where 0 equals no activity and 100 equals total inhibition.

TABLE I

| Example | Concentration μM | % Inhibition |
|---|---|---|
| 1A | 1.00 | 97.98 |
| 1B | 1.00 | 92.70 |
| 2 | 1.00 | 100 |
| 3 | 0.316 | 100 |
| 4 | 0.316 | 82.06 |
| 5 | 1.00 | 100 |
| 6 | 1.00 | 100 |
| 7 | 1.00 | 100 |
| 8 | 1.00 | 100 |
| 9 | 1.00 | 100 |
| 10 | 1.00 | 100 |
| 11 | 1.00 | 59.16 |
| 12 | 1.00 | 78.70 |
| 13 | 1.00 | 31.96 |
| 14 | 15.00 | 31.66 |
| 15 | 3.16 | 100 |
| 16 | 0.316 | 80.00 |
| 17 | 1.00 | 100 |
| 18 | 1.00 | 69.77 |
| 19 | 1.00 | 93.24 |
| 20 | 1.00 | 86.60 |
| 21 | 1.00 | 100 |
| 22 | 0.316 | 40.69 |
| 23 | 0.316 | 76.49 |
| 24 | 0.316 | 4.96 |
| 25 | 0.316 | 35.90 |
| 26A | 0.316 | 82.56 |
| 26B | 0.316 | 76.36 |
| 27 | 0.316 | 44.70 |
| 28 | 0.316 | 78.03 |
| 29 | 0.316 | 56.13 |
| 30 | 0.316 | 38.45 |
| 31 | 0.316 | 82.12 |
| 32 | 1.00 | 81.60 |
| 34 | 1.00 | 94.23 |
| 35 | 1.00 | 76.19 |
| 36 | 150.00 | 43.89 |
| 37 | 1.00 | 39.98 |
| 38 | 1.00 | 34.00 |
| 40 | 0.316 | 25.63 |
| 41 | 15.00 | 58.38 |
| 42 | 0.316 | 10.90 |
| 43 | 0.316 | 11.87 |
| 44 | 0.316 | 5.70 |
| 45 | 3.16 | 72.16 |
| 46 | 15.00 | 69.90 |
| 47 | 0.316 | 49.68 |
| 48 | 0.316 | 4.36 |

TABLE I-continued

| Example | Concentration μM | % Inhibition |
|---|---|---|
| 49 | 0.316 | 65.74 |
| 50A | 0.316 | 83.28 |
| 50B | 0.316 | 83.99 |
| 51 | 1.00 | 95.14 |
| 52 | 1.00 | 71.85 |
| 53 | 0.316 | 74.78 |
| 54 | 0.316 | 73.78 |
| 55 | 0.316 | 17.33 |
| 56 | 0.316 | 74.78 |
| 57 | 0.316 | 66.60 |
| 58 | 0.316 | 65.72 |
| 59 | 0.316 | 71.90 |
| 60 | 0.316 | 86.70 |
| 61 | 0.316 | 61.46 |
| 64 | 0.316 | 91.50 |
| 65 | 0.316 | 95.60 |

It should be understood that the instant specification and examples are set forth by way of illustration and not limitation, and that various modifications and changes may be made without departing from the spirit and scope of the present invention as defined by the appended claims.

We claim:

1. A process of resolving racemates of the 4a,10b-transenantiomers of those compounds having the Formula I

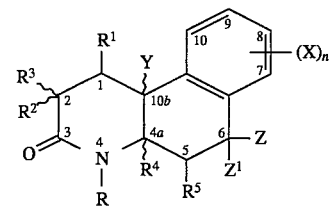

where

R is hydrogen or $C_1$–$C_4$ alkyl;

Z and $Z^1$ are independently selected from hydrogen and $C_1$–$C_4$ alkyl;

Y is hydrogen;

$R^1$, $R^2$, $R^3$, $R^4$ and $R^5$ are all hydrogen;

n is 1 or 2; and

X is hydrogen, halogen, $NO_2$, $CF_3$, $C_1$–$C_6$ alkyl, $C_1$–$C_4$ alkoxy, amino, $C_1$–$C_4$ alkylamino, $C_1$–$C_4$ dialkylamino, mercapto, or $C_1$–$C_6$ alkylthio;

into their component optical isomers comprising essentially the steps of:

(a) contacting a methanol solution of said racemate with a strong acid to afford a 1-(2-methoxycarbonylethyl)-2-(amino)- 1,2,3,4-tetrahydronaphthalene;

(b) contacting said tetrahydronaphthalene from (a) with a methanol solution of an optically active di-p-toluoyltartaric acid to afford a corresponding tetrahydronaphthalene salt; and (c) treating said salt from (b) with a base to obtain a free amine having substantially one optically active isomer;

(d) heating said free amine from (c) at a temperature from about 35° C. to about 120° C. to recyclize and afford the desired octahydrobenzo[f]quinolinone.

2. A salt of di-p-toluoyl-(D) or (L)-tartaric acid and a trans isomer of a compound having the formula

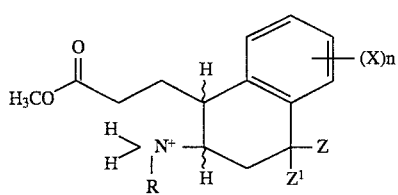
where
R is hydrogen or $C_1$–$C_4$ alkyl;
Z and $Z^1$ are independently selected from hydrogen and $C_1$–$C_4$ alkyl;
n is 1 or 2; and
X is hydrogen, halogen, $NO_2$, $CF_3$, $C_1$–$C_6$ alkyl, $C_1$–$C_4$ alkoxy, amino, $C_1$–$C_4$ alkylamino, $C_1$–$C_4$ dialkylamino, mercapto or $C_1$–$C_6$ alkylthio.
* * * * *